US008309830B2

(12) United States Patent
Ward et al.

(10) Patent No.: US 8,309,830 B2
(45) Date of Patent: Nov. 13, 2012

(54) WHEAT VARIETY MSU LINE E0028

(75) Inventors: Richard W. Ward, Kabul (AF); Lee F. Siler, Merrill, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 337 days.

(21) Appl. No.: 12/763,713

(22) Filed: Apr. 20, 2010

(65) Prior Publication Data

US 2010/0272876 A1 Oct. 28, 2010

Related U.S. Application Data

(60) Provisional application No. 61/171,982, filed on Apr. 23, 2009.

(51) Int. Cl.
*A01H 5/00* (2006.01)
*A01H 5/10* (2006.01)
*A01H 1/00* (2006.01)
*A01H 4/00* (2006.01)
*C12N 15/82* (2006.01)

(52) U.S. Cl. ............... 800/320.3; 800/260; 800/263; 800/264; 800/265; 800/278; 800/279; 800/281; 800/284; 800/286; 800/288; 800/289; 800/300; 800/301; 800/302; 800/303; 435/410

(58) Field of Classification Search .................. None
See application file for complete search history.

(56) References Cited

U.S. PATENT DOCUMENTS

| | | | |
|---|---|---|---|
| 6,989,480 B2 | 1/2006 | Marshall et al. | |
| 7,291,774 B2 | 11/2007 | Marshall et al. | |
| 7,342,157 B2 * | 3/2008 | Lively et al. ............... | 800/320.3 |
| 7,365,253 B2 | 4/2008 | Marshall et al. | |

OTHER PUBLICATIONS

Campbell et al., Registration of 'Hopewell' Wheat, Crop Sci. 41:1638-1639 (2001).
Everson et al., Registration of 'Augusta' Wheat, Crop Sci. 26:201-202 (1986).
Finney and Andrews, Revised Microtesting for Soft Wheat Quality Evaluation, Cereal Chem. 63(3):177-182 (1986).
Fuentes et al., Resource Allocation and Cultivar Stability in Breeding for Fusarium Head Blight Resistance in Spring Wheat, Crop Sci. 45:1965-1972 (2005).
Gaines et al., Developing Agreement Between Very Short Flow and Longer Flow Test Wheat Mills, Cereal Chem. 77(2):187-192 (2000).
Gleeson et al., Residual Maximum Likelihood (REML) Estimation of a Neighbour Model for Field Experiments, Biometrics 43:277-287 (1987).
Griffey et al., Registration of 'McCormick' Wheat, Crop Sci. 45:417-419 (2005).
Griffey et al., Registration of 'Roane' Wheat, Crop Sci. 41:1359-1360 (2001).
Griffey et al., Registration of 'Tribute' Wheat, Crop Sci. 45:419-420 (2005).
Jensen, Registration of 'Arrow' Wheat (Reg. No. 527), Crop Sci. 13(4):495 (1973).
Jensen, Registration of 'Yorkstar' Wheat (Reg. No. 475), Crop Sci. 8:641-642 (1968).
Knott et al., Comparison of Selection Methods for the Development of White-Seeded Lines from Red x White Soft Winter Wheat Crosses, Crop Sci. 48:1807-1816 (2008).
Lewis et al., Registration of 'Ambassador' Wheat, Journal of Plant Registrations 4(3):195-204 (2010).
Patterson and Thompson, Recovery of Inter-Block Information When Block Sizes Are Unequal, Biometrika 58(3):545-554 (1971).
Robinson et al., REML—A Program for the Analysis of Non-Orthogonal Data by Restricted Maximum Likelihood, COMPSTAT: Proceedings in Computational Statistics, Physica-Verlag, Wien, 231-232 (1982).
Schroeder et al., Factors Affecting Resistance of Wheat to Scab Caused by *Gibberella zeae*, Phytopathology 53:831-838 (1963).
Sorrells et al., Registration of 'Caledonia' Wheat, Crop Sci. 44:1471-1472 (2004).

* cited by examiner

*Primary Examiner* — Cynthia Collins
(74) *Attorney, Agent, or Firm* — Harness, Dickey & Pierce, P.L.C.

(57) ABSTRACT

A wheat variety designated MSU Line E0028, the plants and seeds of MSU Line E0028, methods for producing a wheat plant produced by crossing the variety E0028 with another wheat plant, and hybrid wheat seeds and plants produced by crossing the variety E0028 with another wheat line or plant, and the creation of variants by mutagenesis or transformation of variety E0028. The present technology also relates to methods for producing other wheat varieties or breeding lines derived from MSU Line E0028 and to wheat varieties or breeding lines produced by those methods.

34 Claims, No Drawings

WHEAT VARIETY MSU LINE E0028

CROSS-REFERENCE TO RELATED APPLICATIONS

This application claims the benefit of U.S. Provisional Application No. 61/171,982, filed on Apr. 23, 2009. The entire disclosure of the above application is incorporated herein by reference.

GOVERNMENT RIGHTS

This invention was made with support in part by the U.S. Department of Agriculture, under Agreement No. 59-0790-6-061, where the invention is a cooperative project with the U.S. Wheat & Barley Scab Initiative. The U.S. Government has certain rights in the invention.

INTRODUCTION

This invention relates to wheat and more particularly to a variety of soft winter white wheat designated MSU Line E0028, also referred to as "Ambassador."

Wheat is grown worldwide and is a widely adapted cereal. Wheat may be divided into five main market classes, which include the common wheat (*Triticum aestivum* L.) classes: hard red winter, hard red spring, soft red winter, soft and hard white, and durum (*Triticum turgidum* L.). Common wheats are used in a variety of food products, such as bread, cookies, cakes, crackers, and noodles. In general, the hard wheat classes are milled into flour used for breads and the soft wheat classes are milled into flour used in a variety of products, such as pastries, crackers, breakfast cereals and soup thickeners. Wheat starch is used in the food and paper industries, as laundry starches, and in other products.

Grain quality of wheat is very important for its use in baking. To test the grain quality of wheat for use as flour, milling properties are analyzed. Important milling properties include relative hardness or softness, weight per bushel of wheat (test weight), siftability of the flour, break flour yield, middlings flour yield, total flour yield, flour ash content, and wheat-to-flour protein conversion. Good processing quality for flour is also important. Good quality characteristics for flour from soft wheats include low to medium-low protein content, low water absorption, production of large-diameter test cookies and large volume cakes. Wheat glutenins and gliadins, which together confer the properties of elasticity and extensibility, play an important role in the grain quality. Changes in quality and quantity of these proteins change the end product for which the wheat can be used.

Wheat is an important and valuable field crop. Thus, a continuing goal of wheat breeders is to develop stable, high yielding wheat varieties that are agronomically sound and have good grain quality for its intended use. To accomplish this goal, the wheat breeder must select and develop wheat plants that have the traits that result in superior varieties. These selection processes, which ultimately lead to the marketing and distribution of the wheat variety, can take many years from the time the first cross is made. Development of new wheat varieties is therefore a time-consuming process that requires precise forward planning, efficient use of resources, and a minimum of changes in direction.

SUMMARY

The present technology provides seeds of soft winter white wheat variety designated E0028, representative seed of variety E0028 deposited under American Type Culture Collection (ATCC) Patent Deposit Designation PTA-10223, also denominated "Ambassador." The present technology also provides compositions and methods that include, use, or operate on, or are derived from E0028. Such technology includes seeds of MSU Line E0028, whole plants and portions of plants of MSU Line E0028, and methods for producing a wheat plant by crossing MSU Line E0028 with another wheat plant. Products include flour and other refined or isolated materials derived from variety E0028. For example, these include edible products such as baked goods, cereals, pastas, beverages, livestock feeds, energy products such as biofuels, and further include non-edible products such as wheat straw and construction materials produced from MSU Line E0028.

Methods further include developing other wheat varieties or breeding lines derived from MSU Line E0028 and compositions that include the wheat varieties or breeding lines produced by those methods. Creation of variants, by mutagenesis or transformation of MSU Line E0028, is also provided. The present compositions and methods also relate to transgenic backcross conversions of MSU Line E0028.

MSU Line E0028 demonstrates a unique combination of traits, including higher yield (bushels/acre), high flour yield, and increased winter hardiness in comparison to other wheat varieties.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

The headings (such as "Introduction" and "Summary") and sub-headings used herein are intended only for general organization of topics within the present technology, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. All references cited in the "Detailed Description" section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the apparatus and systems of this technology and, unless explicitly stated otherwise, are not intended to be a representation that given embodiments of this technology have, or have not, been made or tested.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. In addition, disclosure of ranges includes disclosure of all distinct values and further divided ranges within the entire range.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, tolerance to drought and heat, improved grain quality, and better agronomic qualities.

Field crops are bred through techniques that take advantage of the plant's method of pollination. A plant is self-pollinated if pollen from one flower is transferred to the same or another flower of the same plant. A plant is sib-pollinated when individuals within the same family or line are used for pollination. A plant is cross-pollinated if the pollen comes from a flower on a different plant from a different family or line. The term cross-pollination herein does not include self-pollination or sib-pollination. Wheat plants (*Triticum aestivum* L.), are recognized to be naturally self-pollinated plants which, while capable of undergoing cross-pollination, rarely do so in nature. As such, intervention for control of pollination is important to the establishment of superior varieties.

A cross between two different homozygous lines produces a uniform population of hybrid plants that may be heterozygous for many gene loci. A cross of two heterozygous plants each that differ at a number of gene loci will produce a population of plants that differ genetically and will not be uniform. Regardless of parentage, plants that have been self-pollinated and selected for type for many generations become homozygous at almost all gene loci and produce a uniform population of true breeding progeny. A homozygous plant is hereby defined as a plant with homozygous genes at 95% or more of its loci. The term "inbred" as used herein refers to a homozygous plant or a collection of homozygous plants.

Choice of breeding or selection methods depends on the mode of plant reproduction, the heritability of the trait(s) being improved, and the type of variety used commercially; e.g., F1 hybrid variety, pure-line variety, etc. For highly heritable traits, a choice of superior individual plants evaluated at a single location can be effective, whereas for traits with low heritability, selection may be based on mean values obtained from replicated evaluations of families of related plants. Popular selection methods commonly include pedigree selection, modified pedigree selection, mass selection, and recurrent selection.

The complexity of inheritance influences choice of the breeding method. In general, breeding starts with the crossing of two genotypes (a "breeding cross"), each of which may have one or more desirable characteristics that is lacking in the other or which complements the other. If the two original parents do not provide all the desired characteristics, other sources can be included by making more crosses. In each successive filial generation, F1→F2; F2→F3; F3→F4; F4→F5, etc., plants are selfed to increase the homozygosity of the line. Typically in a breeding program five or more generations of selection and selfing are practiced to obtain a homozygous plant.

Pedigree breeding is commonly used for the improvement of self-pollinating crops. Two parents that possess favorable, complementary traits are crossed to produce an F1. An F2 population is produced by selfing or sibbing one or several F1's. Selection of the best individuals may begin in the F2 population; then, beginning in the F3, the best individuals in the best families are selected. Replicated testing of families can begin in the F4 generation to improve the effectiveness of selection for traits with low heritability. At an advanced stage of inbreeding (i.e., F5, F6 and F7), the best lines or mixtures of phenotypically similar lines are tested for potential release as new varieties.

Backcross breeding is used to transfer genes for simply inherited, qualitative traits from a donor parent into a desirable homozygous variety that is utilized as the recurrent parent. The source of the traits to be transferred is called the donor parent. After the initial cross, individuals possessing the desired trait or traits of the donor parent are selected and then repeatedly crossed (backcrossed) to the recurrent parent. The resulting plant is expected to have the attributes of the recurrent parent (e.g., variety) plus the desirable trait or traits transferred from the donor parent. This approach has been used extensively for breeding disease resistant varieties.

Each wheat breeding program includes a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful varieties produced per unit of input; e.g., per year, per dollar expended, etc.

Various recurrent selection techniques are used to improve quantitatively inherited traits controlled by numerous genes. The use of recurrent selection in self-pollinating crops depends on the ease of pollination and the number of hybrid offspring from each successful cross. Recurrent selection can be used to improve populations of either self- or cross-pollinated crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued. Plants from the populations can be selected and selfed to create new varieties.

Another breeding method is single-seed descent. This procedure, in the strict sense, refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed. In a multiple-seed procedure, wheat breeders commonly harvest one or more spikes (heads) from each plant in a population and thresh them together to form a bulk. Part of the bulk is used to plant the next generation and part is put in reserve. The procedure has been referred to as modified single-seed descent. The multiple-seed procedure has been used to save labor at harvest. It is considerably faster to thresh spikes with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Bulk breeding can also be used. In the bulk breeding method, an F2 population is grown. The seed from the populations is harvested in bulk and a sample of the seed is used to make a planting the next season. This cycle can be repeated several times. In general when individual plants are expected to have a high degree of homozygosity, individual plants are selected, tested, and increased for possible use as a variety.

Molecular markers, including techniques such as Starch Gel Electrophoresis, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs), may be used in plant breeding methods. One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the markers of the donor parent. Using this procedure can minimize the amount of genome from the donor parent that remains in the selected plants. It can also be used to reduce the number of crosses back to the recurrent parent needed in a backcrossing program (Openshaw et al., Marker-assisted Selection in Backcross Breeding. In: Proceedings Symposium of the Analysis of Molecular Marker Data, 5-6 Aug. 1994, pp. 41-43. Crop Science Society of America, Corvallis, Oreg.). The use of molecular markers in the selection process may be referred to as Marker Assisted Selection or as Genetic Marker Enhanced Selection.

The production of double haploids can also be used for the development of homozygous lines in the breeding program. Double haploids are produced by the doubling of a set of chromosomes (1N) from a heterozygous plant to produce a completely homozygous individual. This can be advantageous because the process omits the generations of selfing needed to obtain a homozygous plant from a heterozygous source. Various methodologies of making double haploid plants in wheat have been developed (Laurie, D. A. and S. Reymondie, Plant Breeding, 1991, v. 106:182-189; Singh, N. et al., Cereal Research Communications, 2001, v. 29:289-296; Redha, A. et al., Plant Cell Tissue and Organ Culture, 2000, v. 63:167-172; and U.S. Pat. No. 6,362,393, Konzak et al., issued Mar. 26, 2002.

Though pure-line varieties are the predominate form of wheat grown for commercial wheat production, hybrid wheat is also used. Hybrid wheats are produced with the help of cytoplasmic male sterility, nuclear genetic male sterility, or chemicals. Various combinations of these three male sterility systems have been used in the production of wheat.

Descriptions of other breeding methods that are commonly used for different traits and crops can be found in one of several reference books; e.g., Allard, Principles of Plant Breeding, 1960; Simmonds, Principles of Crop Improvement, 1979; Heyne, Wheat and Wheat Improvement, 1987; Allan, "Wheat", Chapter 18, Principles of Crop Development, vol. 2, Fehr editor, 1987).

Promising advanced breeding lines are thoroughly tested and compared to appropriate standards in environments representative of the commercial target area(s). The best lines are candidates for new commercial varieties; those still deficient in a few traits may be used as parents to produce new populations for further selection.

A difficult task is the identification of individuals that are genetically superior, because for most traits the true genotypic value is masked by other confounding plant traits or environmental factors. One method of identifying a superior genotype is to observe its performance relative to other experimental genotypes and to a widely grown standard variety. Generally, a single observation is inconclusive, so replicated observations are required to provide a better estimate of its genetic worth.

A breeder uses various methods to help determine which plants should be selected from the segregating populations and ultimately which lines will be used for commercialization. In addition to the knowledge of the germplasm and other skills the breeder uses, a part of the selection process is dependent on experimental design coupled with the use of statistical analysis. Experimental design and statistical analysis are used to help determine which plants, which family of plants, and finally which lines are significantly better or different for one or more traits of interest. Experimental design methods are used to control error so that differences between two lines can be more accurately determined. Statistical analysis includes the calculation of mean values, determination of the statistical significance of the sources of variation, and the calculation of the appropriate variance components. Five and one percent significance levels are customarily used to determine whether a difference that occurs for a given trait is real or due to the environment or experimental error.

Plant breeding is the genetic manipulation of plants. The goal of wheat breeding is to develop new, unique, and superior wheat varieties. In practical application of a wheat breeding program, the breeder initially selects and crosses two or more parental lines, followed by repeated selfing and selection, producing many new genetic combinations. The breeder can theoretically generate billions of different genetic combinations via crossing, selfing, and mutations. The breeder has no direct control at the cellular level. Therefore, two breeders will never develop exactly the same line. Each year, the plant breeder selects the germplasm to advance to the next generation. This germplasm is grown under unique and different geographical, climatic and soil conditions; and further selections may then be made during and at the end of the growing season.

Proper testing should detect major faults and establish the level of superiority or improvement over current varieties. In addition to showing superior performance, there must be a demand for a new variety. The new variety must be compatible with industry standards, or must create a new market. The introduction of a new variety may incur additional costs to the seed producer, the grower, processor and consumer, for special advertising and marketing, altered seed and commercial production practices, and new product utilization. The testing preceding release of a new variety should take into consideration research and development costs as well as technical superiority of the final variety. It must also be feasible to produce seed easily and economically.

A wheat variety needs to be highly homogeneous, homozygous, and reproducible to be useful as a commercial variety. There are many analytical methods available to determine the homozygotic stability, phenotypic stability, and identity of these varieties. The oldest and most traditional method of analysis is the observation of phenotypic traits. This type of data is usually collected in field experiments over the life of the wheat plants to be examined. Phenotypic characteristics observed include traits such as seed yield, head configuration, glume configuration, seed configuration, lodging resistance, disease resistance, and maturity, among others.

In addition to phenotypic observations, the genotype of a plant can also be examined. There are many laboratory-based techniques available for the analysis, comparison, and characterization of a plant genotype; among these are Gel Electrophoresis, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). Gel electrophoresis is particularly useful in wheat. For example, wheat variety identification is possible through electrophoresis of gliadin, glutenin, albumin and globulin, and total protein extracts (Bietz, J. A. 1987, Genetic and biochemical studies of nonenzymatic endosperm proteins, In E. G. Heyne (ed.) Wheat and Wheat Improvement, ASA, Madison Wis., pp. 215-241).

The present technology relates to a new and distinctive wheat variety, designated E0028, also referred to as "Ambassador," which is the result of years of careful breeding and selection as part of a wheat breeding program. Variety E0028, is semi-dwarf soft white winter wheat (*Triticum aestivum* L.) developed at Michigan State University (MSU). E0028 was selected from a cross of Pioneer Brand 2737W/D1148 made in 1994 at MSU. The cultivar is an $F_7$ derived line, and the original experimental number with MSU is E0028. In addition to standard yield test criteria, milling and baking performance was also considered for selection. E0028 was released because of its excellent grain yield, flour yield, and good winter hardiness. Disadvantages may include low test weight, and susceptibility to *Fusarium* head blight (*Fusarium graminearum* Schwabe) and associated deoxynivalenol (DON) accumulation with respect to other entries in the Michigan State Performance Trial. E0028 is well adapted to Michigan and Ontario, Canada, and has also produced high yields throughout the region. The name "Ambassador" was chosen because the cultivar's performance excels in both the U.S. (Michigan) and Canada (Ontario), bringing together white wheat growers on both sides of the border.

E0028 was selected from the cross Pioneer Brand '2737W' (PI# 561197)/D1148 made in 1994 at MSU. 2737W is a soft white winter wheat developed by Pioneer Hi-Bred International, Inc. (Johnston, Iowa). D1148 is a soft white winter wheat developed by MSU with the pedigree 12214/B0246//'Yorkstar' (Jensen, 1968, Registration of 'Yorkstar' Wheat (Reg. No. 475). Crop Sci. 8: 641-b-642-b)/3/'Augusta' (Everson et al, 1986, Registration of 'Augusta' wheat. Crop Sci. 26:201-202)/4/'Asosan' (CI# 12665)/4*'Genessee' (CI# 12653)//'Arrow'(Jensen, 1973, Registration of 'Arrow' Wheat. Crop Sci 13(4):495).

E0028 was developed using a modified bulk breeding method. The cross between the two parents, designated as cross population 940310, was made in the greenhouse in spring 1994. The $F_1$ was advanced in the greenhouse in fall 1994. The $F_1$ and $F_2$ were bulk harvested and planted in single drill plots (7 rows, 15.2 cm spacing, and 2.74 m long) in the field in Mason, Mich. in fall 1995 and 1996, respectively. From the $F_3$ drill plot, $F_4$ seed was bulk harvested and planted in one space planted field plot (15.24 m long, 4 rows, 17.8 cm spacing between seeds within rows) in fall 1997. From the $F_4$ plot, forty heads were selected (see criteria for selection below) and planted as $F_5$ headrows in fall 1998. Fourteen $F_5$ headrows were selected and sampled for three to seven heads, which were planted as $F_6$ headrows in fall 1999. The remainder of the plants in the selected $F_5$ headrows was bulk harvested (by headrow) and planted as $F_6$ drill plots in fall 1999. One $F_6$ drill plot (entry 155), corresponding with five $F_6$ headrows (the drill plot and headrows all derived from a single $F_5$ headrow), was harvested and planted for the 2001 Preliminary Yield Trial (PYT) under the experimental line designation E0028. Three of the five corresponding $F_6$ headrows were bulk harvested individually and space-planted as three $F_7$ plots in fall 2000. From each of the $F_7$ plots (experimental names E0028-1, E0028-2 and E0028-3), individual plants were harvested and each plant was used to sow a single plant derived space planted $F_{7:8}$ plots (15.24 m long, 4 rows, 17.8 cm spacing between seeds within rows) in fall 2001. The remainder of the E0028-2 $F_7$ plot was bulk harvested and used to plant the 2002 Advanced Yield Trial (AYT). One $F_{7:8}$ single plant derived space planted plot was selected, from which two plants were harvested and planted as $F_{7:9}$ space planted plots with the experimental name E0028-R6. In addition, a bulk of the remainder of the $F_{7:8}$ single plant derived space planted plot was planted in the 2003 AYT. From the two $F_{7:9}$ plots, ten individual plants were selected and planted as $F_{7:10}$ space planted plots. The remainder of plants in the $F_{7:9}$ plots were bulk harvested and planted as $F_{7:10}$ plants in the 2004 Michigan State Performance Trial (MSPT). Four of the ten $F_{7:10}$ single plant derived space planted plots were selected. From these four plots, nineteen plants were harvested and planted as $F_{7:11}$ single plant derived space planted plots planted in fall 2004, and the remainder of the plots were bulk harvested and planted as $F_{7:11}$ in the 2005 MSPT under experimental name E0028-R6. From the nineteen $F_{7:11}$ single plant derived space planted plots, sixteen were selected and bulk harvested. This bulk was used to plant an $F_{7:12}$ increase and purification in Colorado in 2005. A bulk of E0028-R6 was used to plant the $F_{7:12}$ in the 2006 MSPT. In 2006, the seed increase from Colorado was used to plant the $F_{7:13}$ for a second increase in Colorado, as well as the 2007 MSPT, Uniform Eastern Soft Red Winter Wheat Nursery (UESRWWN), and OPT. The 2007 Colorado seed increase was used to plant the 2008 MSPT and OPT.

E0028 (E0028, E0028-2 and E0028-R6) was included in the following replicated yield trials harvested in 2001 through 2008: PYT (2001), AYT (2002 and 2003), MSPT (2004 through 2008). Yield trial plots were planted in the following manner: All yield trials were planted in six locations in various counties around the State of Michigan. Plot size was 3.4 m long, 7 rows, 15.24 cm row spacing for 2001 and 2002, but 3.7 m long, 7 rows, 15.24 cm row spacing in 2003 and 2004, and 3.7 m long, 6 rows, 19 cm row spacing from 2005 onward. Trials were four replication alpha-lattice designs at each site, except the 2001 PYT, which was planted as a three replication alpha-lattice design at each site. For the 2001 through 2004 yield trials, seeding rates were the equivalent of a solid stand of 4.45 million seeds per hectare in 15.24 cm rows. For the 2005 yield trial onward, seeding rates were increased to 4.94 million seeds per hectare in a solid stand planted in 19.95 cm rows. Fall fertilizer application varied by cooperator practice, and spring nitrogen was applied as urea (100.9 kg ha$^{-1}$ actual N). No foliar fungicides were applied and weeds and insects were controlled as needed with Harmony™ Extra and Lannate™, respectively. Yield trial plots were harvested on a single day according to site, except for one location in 2008, but analysis of the 2008 data revealed that the different harvest days did not negatively impact yield or test weight data for that site. For 2003, 2006 and 2008, one, one and two yield trial sites, respectively, were not harvested because of various problems with those sites. Yield was calculated using the entire area of the plot including the wheel tracks between plots, a calculation that tends to underestimate the total yield. One location was not harvested in 2006 due to atypical lodging, and two locations were abandoned in 2008 due to severe ice and water damage. Yield and test weight data were collected for all harvested locations, and all replications of the MSPT in each year. Other data were recorded opportunistically, as the traits were apparent in some years and not others. For each year that trait data were collected, at least two replications were observed in at least two locations, with the exception of BYDV, which was observed in only one location in 2007. Since grain color is a major distinction between varieties in the trial, grain color was also recorded.

Selection prior to the $F_7$ was based on visual evaluation of winter survival, plant height, grain appearance (including resistance to black point, *Alternaria* spp. and various fungi), general adult plant reaction to powdery mildew [*Blumeria graminis* (DC.) E. O, Speer], Wheat spindle streak mosaic virus (WSSMV), leaf blotches [causal organisms were not specifically identified, but were likely a combination of *Stagonospora nodorum* (Berk.) Castellani & E. G. Germano and *Septoria tritici* Roberge in Desmaz], leaf rust [*P. recondita* Roberge ex Desmaz. f. sp. *tritici* (Eriks. & E. Henn.) D. M. Henderson], lodging and maturity. Selection of all of these traits, with the exception of height, grain appearance and maturity, were very influenced by environmental pressures that could be present in some years and not others. Hence, selection for many of these traits was opportunistic according to the conditions in each year. From the $F_7$ onward, E0028 was evaluated in replicated multi-location yield trials in Michigan, where milling and baking performance were employed as criteria for selection in addition to standard yield test criteria.

At the seedling stage, E0028 has white/clear (no anthocyanins) coleoptiles, semiprostate juvenile plant growth habit, glabrous with medium green lower leaf blades and medium tillering capacity at low densities. At boot stage, flag leaves are medium green and glabrous (some waxiness on lower side) of medium width and medium length, slightly recurved with green and slightly pubescent auricles, and has a flag leaf sheath that is glabrous with a somewhat waxy bloom. At maturity, E0028 is of medium height (90.5 cm, not significantly different from the MSPT trial mean of 89 cm, $LSD_{p<0.05}$=3.5 cm, Table 15), with straight culms with a slightly waxy and glabrous upper internode, is slightly pubescent on margins of the rachis, and has thick walled white colored straw. The spike is white, awnletted, inclined, oblong in shape with pronounced waxy bloom and is medium in length and density; awns are shorter than the spike and white. Glumes are glabrous and of medium width and length with oblique shoulders and medium length obtuse beaks. E0028 has kernels that are soft white, oval to ovate in shape, rounded cheek shape, medium brush with midlong brush hairs.

Variety E0028 is adapted to Michigan, USA and Ontario, Canada. It demonstrates a higher yield in bushels per acre and increased winter hardiness versus other wheat varieties tested in the Michigan State Performance Trial. E0028 demonstrates good milling and baking qualities, with higher than average flour yield. Softness equivalent percent and percent protein in flour are average. Lactic acid retention is lower than average. E0028 is lower than average for black point (*Alternaria* spp.).

In comparison with other varieties tested in Michigan, E0028 shows average performance to leaf rust (*Puccinia recondita* f.sp. *tritici*), powdery mildew (*Erysiphe graminis* f.sp. *tritici*), leaf blotch (likely a combination of *Stagonospora tritici* and *Stagonospora nodorum*), and wheat spindle streak mosaic virus. Winter kill, plant height, flowering time, and lodging susceptibility are also average.

The primary weaknesses of E0028 include lower than average test weight and susceptibility to *Fusarium* head blight (*Fusarium graminearum*) and associated deoxynivalenol (DON) accumulation. However, *Fusarium* head blight visual symptoms (incidence, severity, and index) are not statistically different from average. E0028 also exhibits higher than average pre-harvest sprouting, as compared to other wheat varieties.

E0028 has been found to be uniform and stable in its performance in replicated yield trials, including over four years of MSPTs. E0028 remains essentially unchanged in its primary and distinctive characteristics following sexual reproduction. It has self-pollinated a sufficient number of generations, with careful attention to uniformity of plant type, to ensure homozygosity and phenotypic stability. The line has been increased with continued observation for uniformity. No substantial variant traits are observed or are expected in E0028. Since E0028 is substantially homozygous, it may be reproduced by planting seeds of the line, growing the resulting wheat plants under self-pollinating or sib-pollinating conditions, and harvesting the resulting seed, using techniques familiar to the agricultural arts. Variants, though infrequent, have been observed as follows: brown chaff <0.03%, extreme tails <0.05%, bearded <0.06%, red seed <0.5%. These variants are at commercially acceptable levels.

The yield of E0028 is slightly better over a 4 year average, though not significant, than the white wheat variety known as "Calcdonia." Calcdonia (Reg. no. CV-943, PI 610188) is a soft white winter wheat (*Triticum aestivum* L.) developed by the Cornell Agricultural Experiment Station (Cornell Univ., Ithaca, N.Y.) that exhibits high grain yield and wide-adaptation in the northeastern USA and southern Ontario, Canada. Variety E0028 exhibits good winter hardiness in comparison to Calcdonia and grows about 2 inches taller than Calcdonia.

Selection characteristics for E0028 include higher yield (bushels/acre), higher flour yield, and an increase in winter hardiness, in comparison to averages of other wheat varieties, including D8006W, Crystal, Jewel, Aubrey, Pioneer Brand 25W41, and Calcdonia. However, E0028 exhibits lower than average test weight and higher than average DON in the grain, as compared to averages of the other wheat varieties.

The early harvest test weight of variety E0028 can be ascertained to determine whether the test weight of E0028 is improved by earlier harvesting. The following method is used to examine the early harvest test weight. Sub-samples of 3 feet (out of 12 foot plots) from quality trials at 5 yield testing sites are manually harvested. A single replication is harvested at each of the five locations. E0028 is harvested, as well as four other varieties for comparison. These samples are harvested between 2 and 6 days earlier than the regular harvest for the site. Early harvested samples are threshed and run through a moisture and test weight machine the same day as harvest, then placed on driers at Michigan State University's wheat barn.

The remainder of the quality trial plots (9 feet) is used for early harvest, plus the quality trial plots at the 6th yield testing site (12 feet—not used for early harvest) are harvested at the regular harvesting time using a combine. These samples are also dried on the drier. Dried samples of the early harvest and the regular harvest from the quality trial plots are sent to Star of the West Milling (Frankenmuth, Mich.) for testing of falling number and DON levels.

Characteristics of MSU Line E0028 are summarized and categorized according to the several data types presented in the Tables below. Several entries are included for comparison, including MSU releases (MSU D8006W, MSU E0027, MSU E1007W) in addition to widely grown varieties, such as Calcdonia. All entries are white wheat. Where applicable, significant differences in comparison with E0028 are denoted as "S+" for a value significantly more than E0028 (LSD 0.05), or as "S-" for a value significantly less than E0028 (LSD 0.05). Breeder interpretation is needed to consider whether higher (S+) or lower (S-) values for a trait are desirable.

TABLE 1

E0028 Early Harvest Test Weight

| Name | TEST WEIGHTS | | % MOISTURE | | PPM DON | | FALLING NUMBER | |
|---|---|---|---|---|---|---|---|---|
| | Normal Harvest 2007 | Early Harvest 2007 | Normal Harvest 2007 | Early Harvest 2007 | Normal Harvest 2007 | Early Harvest 2007 | Normal Harvest 2007 | Early Harvest 2007 |
| MSU Line E0028 | 57.3 | 57.6 | 12.4 | 16.1 | 0.11 | 0.20 | 311 | 317 |
| Crystal (MSU E0027) | 58.0 | 56.4 | 12.1 | 18.1 | 0.27 | 0.38 | 329 | 324 |
| AC Mountain | 57.3 | 54.8 | 12.8 | 18.8 | 0.17 | 0.32 | 334 | 340 |
| Aubrey | 59.5 S+ | 58.7 | 13.2 S+ | 16.1 | <0.1 | 0.11 | 351 | 326 |
| Caledonia | 57.4 | 54.8 | 12.9 | 18.4 | 0.44 | 0.48 | 330 | 334 |
| MEANS | 58.4 | 56.1 | 13.4 | 17.8 | 0.31 | 0.30 | 338 | 333 |
| LSD (0.05) | 0.9 | — | 0.8 | — | — | — | — | — |
| CV (%) | 1.4 | — | 5.1 | — | — | — | — | — |

S+ = significantly more than E0028 (LSD 0.05)
S- = significantly less than E0028 (LSD 0.05)
DON = deoxynivalenol

TABLE 2

Source of Samples relating to Early Harvest Test Weight in Table 1.

| Trait | Regular Harvest | Early Harvest |
|---|---|---|
| Test Weight | State Performance Trial Plots (4 reps, 6 sites) | Subsample of quality trial plots (1 rep, 5 sites) |
| Moisture | State Performance Trial Plots (4 reps, 6 sites) | Subsample of quality trial plots (1 rep, 5 sites) |
| DON (ppm) | Remainder of quality trial plots (1 rep, 6 sites) | Subsample of quality trial plots (1 rep, 5 sites) |
| Falling Number | Remainder of quality trial plots (1 rep, 6 sites) | Subsample of quality trial plots (1 rep, 5 sites) |

Tables 3 through 13 present analysis of data from the normal harvest times for the State Performance Trial and the *Fusarium* Head Blight (FHB) screening nursery. These trials are performed by the Department of Crop and Soil Sciences, College of Agriculture and Natural Resources at Michigan State University, East Lansing, Mich. Data from the Wheat Performance Trials is categorized by year and is available online at [www.css.msu.edu/varietytrials/wheat/Variety_Results.html].

TABLE 3

Single and Multiyear Harvest Data Averages - Data from MSU Wheat State Performance Trials
(4 reps per site, see parentheses for the number of sites each year).

Test Weight: lbs/Bushel

| | Single Year Data: 4 reps/site | | | | Multi-Year Averages | | |
|---|---|---|---|---|---|---|---|
| Name | (6 sites) 2007 | (5 sites) 2006 | (6 sites) 2005 | (6 sites) 2004 | 2 YR 06-07 | 3 YR 05-07 | 4 YR 04-07 |
| MSU Line E0028 | 57.3 | 56.4 | 57.3 | 53.6 | 56.9 | 57.0 | 56.2 |
| MSU D8006W | 58.1 | 56.0 | 57.8 | 53.7 | 57.1 | 57.3 | 56.4 |
| Crystal (MSU E0027) | 58.0 | 56.1 | 57.4 | 5.2 S+ | 57.1 | 57.2 | 56.7 |
| Jewel (MSU E1007W) | 59.1 S+ | 57.3 | 59.3 S+ | 56.1 S+ | 58.2 S+ | 58.6 S+ | 58.0 S+ |
| Aubrey | 59.5 S+ | 58.9 S+ | 59.8 S+ | 58.4 S+ | 59.2 S+ | 59.4 S+ | 59.2 S+ |
| Pioneer Brand 25W41 | 59.2 S+ | 57.4 S+ | 60.0 S+ | 56.7 S+ | 58.3 S+ | 58.9 S+ | 58.3 S+ |
| Caledonia | 57.4 | 56.3 | 58.7 S+ | 54.8 | 56.9 | 57.5 | 56.8 |
| Trial Mean | 58.4 | 57.4 | 58.9 | 56.7 | 58.2 | 58.5 | 58.1 |
| LSD (0.05) | 0.9 | 1.0 | 0.8 | 1.3 | 1.0 | 1.0 | 1.1 |
| CV (%) | 1.4 | 1.3 | 1.3 | 2.0 | 0.9 | 1.0 | 1.4 |

S+ = significantly more than E0028 (LSD 0.05)
S− = significantly less than E0028 (LSD 0.05)

TABLE 4

Single and Multiyear Harvest Data Averages - Data from MSU Wheat State Performance Trials
(4 reps per site, see parentheses for the number of sites each year).

Yield: Bushels/Acre (Adjusted to 13% Moisture)

| | Single Year Data: 4 reps/site | | | | Multi-Year Averages | | |
|---|---|---|---|---|---|---|---|
| Name | (6 sites) 2007 | (5 sites) 2006 | (6 sites) 2005 | (6 sites) 2004 | 2 YR 06-07 | 3 YR 05-07 | 4 YR 04-07 |
| MSU Line E0028 | 94.0 | 99.5 | 82.2 | 72.0 | 96.8 | 91.9 | 86.9 |
| MSU D8006W | 94.6 | 97.9 | 80.8 | 74.6 | 96.3 | 91.1 | 87.0 |
| Crystal (MSU E0027) | 93.3 | 97.1 | 82.2 | 69.4 | 95.2 | 90.9 | 85.5 |
| Jewel (MSU E1007W) | 91.3 | 94.6 | 80.6 | 75.5 | 93.0 | 88.8 | 85.5 |
| Aubrey | 87.9 S− | 87.8 | 83.2 | 75.1 | 87.9 S− | 86.3 S− | 83.5 |
| Pioneer Brand 25W41 | 88.3 S− | 93.4 | 79.1 | 69.9 | 90.9 S− | 86.9 | 82.7 |
| Caledonia | 83.1 S− | 94.8 | 79.6 | 70.2 | 89.0 S− | 85.8 S− | 81.9 |
| Trial Mean | 87.7 | 90.9 | 80.0 | 72.8 | 90.3 | 87.5 | 84.1 |
| LSD (0.05) | 4.1 | 7.0 | 4.3 | 4.6 | 5.1 | 5.4 | 5.7 |
| CV (%) | 4.1 | 6.2 | 4.7 | 5.6 | 2.8 | 3.8 | 4.8 |

S+ = significantly more than E0028 (LSD 0.05)
S− = significantly less than E0028 (LSD 0.05)

TABLE 5

Single and Multiyear Harvest Data Averages - Samples collected from inoculated FHB screening trial and analyzed via ELISA at MSU unless otherwise noted.

DON (ppm) in grain

| | Single Year Data | | | | Multi-Year Averages** | |
|---|---|---|---|---|---|---|
| | | | | | | 3 YR |
| Name | 2006 | 2005 | 2004 | 2006 GCMS* | 2 YR 05-06 | 04-06 |
| MSU Line E0028 | 9.0 | 4.0 | 13.5 | 5.6 | 6.5 | 8.8 |
| MSU D8006W | 5.6 S− | 10.5 S+ | 14.5 | 5.2 | 8.1 | 10.2 |
| Crystal (MSU E0027) | 5.5 S− | 8.6 S+ | 10.0 S− | 4.5 | 7.1 | 8.0 |
| Jewel (MSU E1007W) | 9.3 | 8.0 | 14.0 | 6.5 | 8.7 | 10.4 |
| Aubrey | 4.2 S− | 4.8 | 9.0 S− | 3.0 S− | 4.5 | 6.0 S− |
| Pioneer Brand 25W41 | 4.8 S− | 9.0 S+ | 10.5 | 3.1 S− | 6.9 | 8.1 |
| Caledonia | 4.5 S− | 5.3 | 10.5 | 3.3 S− | 4.9 | 6.8 |
| Trial Mean | 3.1 | 3.1 | 7.2 | 2.3 | 3.3 | 4.6 |
| LSD (0.05) | 2.0 | 4.1 | 3.3 | 1.5 | 2.8 | 2.4 |
| CV (%) | 32.1 | 58.3 | 23.2 | 31.9 | 40.7 | 31.3 |

S+ = significantly more than E0028 (LSD 0.05)
S− = significantly less than E0028 (LSD 0.05)

TABLE 6

Single and Multiyear Harvest Data Averages - Field observations in inoculated FHB Screening Nursery unless otherwise indicated.

FHB Incidence (% of spikes)

| | Single Year Data | | | | Multi-Year Averages | |
|---|---|---|---|---|---|---|
| Name | 2007 | 2006 | 2005 | 2004* | 2 YR 06-07 | 3 YR 05-07 |
| MSU Line E0028 | 59.3 | 60.0 | 57.7 | 90.0 | 59.7 | 59.0 |
| MSU D8006W | 62.8 | 60.0 | 80.0 | 80.0 | 61.4 | 67.6 |
| Crystal (MSU E0027) | 43.2 | 35.0 S− | 83.8 | 79.0 | 39.1 S− | 54.0 |
| Jewel (MSU E1007W) | 70.7 | 70.0 | 62.9 | 75.0 S− | 70.4 | 67.9 |
| Aubrey | 59.1 | 50.0 | 64.4 | 86.0 | 54.6 | 57.8 |
| Pioneer Brand 25W41 | 66.1 | 40.0 | 77.5 | 83.0 | 53.1 | 61.2 |
| Caledonia | 56.3 | 50.0 | 60.7 | 82.0 | 53.2 | 55.7 |
| Trial Mean | 54.7 | 41.5 | 66.5 | 82.0 | 49.2 | 55.2 |
| LSD (0.05) | 21.8 | 21.7 | 22.1 | 14.0 | 16.3 | 17.0 |
| CV (%) | 20.5 | 26.2 | 20.8 | 8.0 | 16.4 | 18.9 |

*In 2004 data were combined between the inoculated trial and a naturally infected site.
S+ = significantly more than E0028 (LSD 0.05)
S− = significantly less than E0028 (LSD 0.05)

TABLE 7

Single and Multiyear Harvest Data Averages - Field observations in inoculated FHB Screening Nursery unless otherwise indicated.

FHB Severity (% within spikes)

| | Single Year Data | | | | Multi-Year Averages | |
|---|---|---|---|---|---|---|
| Name | 2007 | 2006 | 2005 | 2004* | 2 YR 06-07 | 3 YR 05-07 |
| MSU Line E0028 | 45.8 | 60.0 | 37.8 | 83.0 | 52.9 | 47.9 |
| MSU D8006W | 52.6 | 50.0 | 50.4 | 74.0 | 51.3 | 51.0 |
| Crystal (MSU E0027) | 67.3 S+ | 40.0 S− | 58.0 | 60.0 S− | 53.7 | 55.1 |
| Jewel (MSU E1007W) | 57.9 | 45.0 | 43.8 | 60.0 S− | 51.5 | 48.9 |
| Aubrey | 35.5 | 45.0 | 29.2 | 76.0 | 40.3 | 36.6 |
| Pioneer Brand 25W41 | 36.3 | 40.0 S− | 56.5 | 61.0 S− | 38.2 | 44.3 |
| Caledonia | 55.8 | 65.0 | 60.3 | 75.0 | 60.4 | 60.4 |
| Trial Mean | 43.6 | 41.2 | 36.8 | 69.0 | 42.1 | 42.3 |
| LSD (0.05) | 21.0 | 16.4 | 24.0 | 16.0 | 15.9 | 13.7 |
| CV (%) | 24.2 | 20.0 | 40.1 | 11.3 | 18.7 | 19.8 |

*In 2004 data were combined between the inoculated trial and a naturally infected site.
S+ = significantly more than E0028 (LSD 0.05)
S− = significantly less than E0028 (LSD 0.05)

TABLE 8

Single and Multiyear Harvest Data Averages - Field observations in inoculated FHB Screening Nursery unless otherwise indicated.

FHB Index (% overall infection)

| | Single Year Data | | | | Multi-Year Averages | |
|---|---|---|---|---|---|---|
| Name | 2007 | 2006 | 2005 | 2004* | 2 YR 06-07 | 3 YR 05-07 |
| MSU Line E0028 | 27.2 | 36.0 | 23.5 | 68.8 | 31.6 | 28.9 |
| MSU D8006W | 35.6 | 30.0 | 39.6 | 50.7 | 32.8 | 35.1 |
| Crystal (MSU E0027) | 30.8 | 14.0 S− | 47.6 | 44.4 | 22.4 | 30.8 |
| Jewel (MSU E1007W) | 41.0 | 31.5 | 24.5 | 52.1 | 36.3 | 32.3 |
| Aubrey | 22.3 | 23.0 | 17.3 | 19.2 | 22.7 | 20.9 |
| Pioneer Brand 25W41 | 24.5 | 16.0 S− | 43.4 | 59.2 | 20.3 | 28.0 |
| Caledonia | 33.0 | 37.0 | 36.3 | 68.3 | 35.0 | 35.4 |
| Trial Mean | 25.3 | 18.1 | 25.0 | 50.5 | 21.9 | 24.2 |
| LSD (0.05) | 19.9 | 16.0 | 18.7 | 29.6 | 12.7 | 12.0 |
| CV (%) | 39.6 | 44.0 | 45.7 | 27.9 | 28.6 | 30.4 |

*In 2004 FHB index data was calculated from a naturally infected site.
S+ = significantly more than E0028 (LSD 0.05)
S− = significantly less than E0028 (LSD 0.05)

TABLE 9

Multiyear Harvest Data Averages - Data from MSU Wheat State Performance Trials.

Milling and Baking Properties (04-06)

| Name | Percent Flour Yield Multi-Year Averages | | Percent Protein In Flour Multi-Year Averages | | Lactic Acid Retention Multi-Year Averages | |
|---|---|---|---|---|---|---|
| | 2 YR 05-06 | 3 YR 04-06 | 2 YR 05-06 | 3 YR 04-06 | 2 YR 05-06 | 3 YR 04-06 |
| MSU Line E0028 | 73.3 | 73.1 | 7.8 | 7.5 | 93.6 | 97.9 |
| MSU D8006W | 73.3 | 73.2 | 8.2 | 7.6 | 112.7 S+ | 114.5 S+ |
| Crystal (MSU E0027) | 72.8 | 72.4 | 7.7 | 7.4 | 101.0 | 104.4 S+ |
| Jewel (MSU E1007W) | 72.0 S− | 71.8 S− | 8.0 | 7.4 | 106.7 S+ | 108.8 S+ |
| Aubrey | 71.7 S− | 72.2 S− | 8.5 S+ | 8.1 S+ | 103.6 S+ | 104.7 S+ |
| Pioneer Brand 25W41 | 70.9 S− | 70.9 S− | 7.6 | 7.4 | 94.2 | 94.8 |
| Caledonia | 72.4 S− | 72.3 | 7.9 | 7.5 | 97.5 | 98.4 |
| Trial Mean | 71.4 | 71.2 | 8.0 | 7.6 | 102.4 | 103.9 |
| LSD (0.05) | 0.9 | 0.9 | 0.7 | 0.5 | 7.9 | 4.9 |
| CV (%) | 0.6 | 0.7 | 4.0 | 4.0 | 3.8 | 2.8 |

S+ = significantly more than E0028 (LSD 0.05)
S− = significantly less than E0028 (LSD 0.05)

TABLE 10

Multiyear Harvest Data Averages - Data from MSU Wheat State Performance Trials.

Milling and Baking Properties (04-06)

| Name | Softness Equivalent Percent Multi-Year Averages | | Quality Lab Test Weight Multi-Year Averages | | Black Point % | |
|---|---|---|---|---|---|---|
| | 2 YR 05-06 | 3 YR 04-06 | 02 YR 5-06 | 3 YR 04-06 | 2006 HARVEST | 2 YR 05-06 |
| MSU Line E0028 | 57.9 | 57.9 | 61.2 | 61.1 | 2.5 | 6.6 |
| MSU D8006W | 59.7 | 59.5 | 61.2 | 61.2 | 26.1 S+ | 25.8 S+ |
| Crystal (MSU E0027) | 59.0 | 58.0 | 61.3 | 61.5 | 1.2 | 3.4 |
| Jewel (MSU E1007W) | 57.2 | 57.3 | 61.8 | 61.8 | 3.2 | 5.6 |
| Aubrey | 58.4 | 58.7 | 62.9 S+ | 62.9 S+ | 7.5 | 9.1 |
| Pioneer Brand 25W41 | 63.0 S+ | 62.1 S+ | 62.3 S+ | 62.3 S+ | 16.9 S+ | 17.5 S+ |
| Caledonia | 60.2 | 60.4 | 61.5 | 61.4 | 5.1 | 8.4 |
| Trial Mean | 58.6 | 58.6 | 62.4 | 62.4 | 10.4 | 12.6 |
| LSD (0.05) | 3.2 | 2.6 | 1.1 | 0.8 | 9.2 | 6.0 |
| CV (%) | 2.7 | 2.7 | 0.9 | 0.8 | 54.8 | 23.3 |

S+ = significantly more than E0028 (LSD 0.05)
S− = significantly less than E0028 (LSD 0.05)

TABLE 11

Multiyear Harvest Data Averages - Data from MSU Wheat State Performance Trials (years included are indicated).

| Name | Percent Grain Moisture at Harvest 4 YR 04-07 | Lodging Score (0-9); (0 = none) 3 YR 04-06 | Flowering Date (Days Past Jan. 1) 3 YR 05-07 | Plant Height (Inches) 3 YR 05-07 | Grain Color | Chaff Color | Awns |
|---|---|---|---|---|---|---|---|
| MSU Line E0028 | 13.3 | 3.5 | 152.0 | 36.3 | WHITE | WHITE | NO |
| MSU D8006W | 13.4 | 4.0 | 152.2 | 36.5 | WHITE | WHITE | YES |
| Crystal (MSU E0027) | 13.0 | 2.5 | 153.0 S+ | 35.4 | WHITE | WHITE | YES |
| Jewel (MSU E1007W) | 14.1 S+ | 3.0 | 152.2 | 36.4 | WHITE | WHITE | YES |
| Aubrey | 14.8 S+ | 2.7 | 151.7 | 36.6 | WHITE | WHITE | NO |
| Pioneer Brand 25W41 | 14.1 S+ | 3.6 | 152.2 | 34.3 S− | WHITE | WHITE | YES |
| Caledonia | 13.9 S+ | 3.6 | 152.7 | 34.3 S− | WHITE | WHITE | NO |

TABLE 11-continued

Multiyear Harvest Data Averages - Data from MSU Wheat State Performance Trials (years included are indicated).

| Name | Percent Grain Moisture at Harvest 4 YR 04-07 | Lodging Score (0-9); (0 = none) 3 YR 04-06 | Flowering Date (Days Past Jan. 1) 3 YR 05-07 | Plant Height (Inches) 3 YR 05-07 | Grain Color | Chaff Color | Awns |
|---|---|---|---|---|---|---|---|
| Trial Mean | 14.4 | 4.1 | 152.2 | 35.8 | | | |
| LSD (0.05) | 0.5 | 1.9 | 0.8 | 1.3 | | | |
| CV (%) | 2.6 | 28.6 | 1.0 | 2.2 | | | |

S+ = significantly more than E0028 (LSD 0.05)
S− = significantly less than E0028 (LSD 0.05)

TABLE 12

Multiyear Harvest Data Averages - Data from MSU Wheat State Performance Trials (years included are indicated).

| Name | Leaf Rust Score (0-9) 3 YR 05-07 | Powdery Mildew Score (0-9) 3 YR 05-07 | Leaf Blotch Score (0-9) 3 YR 04-06 | In Head Sprouting Score (0-9) 3 YR 05-07 |
|---|---|---|---|---|
| MSU Line E0028 | 3.8 | 2.8 | 4.1 | 8.7 |
| MSU D8006W | 3.2 | 1.8 | 3.9 | 7.3 |
| Crystal (MSU E0027) | 2.6 | 1.9 | 4.2 | 8.4 |
| Jewel (MSU E1007W) | 2.9 | 3.1 | 3.4 | 8.3 |
| Aubrey | 3.0 | 1.3 S− | 3.5 | 8.5 |
| Pioneer Brand 25W41 | 2.2 S− | 5.4 S+ | 3.5 | 6.7 S− |
| Caledonia | 4.2 | 3.5 | 3.9 | 8.7 |
| Trial Mean (2007 = 67 Entries) | 3.1 | 2.6 | 3.7 | 5.9 |
| LSD (0.05) | 1.4 | 1.2 | 1.0 | 1.7 |
| CV (%) | 28.2 | 26.8 | 16.1 | 17.8 |

S+ = significantly more than E0028 (LSD 0.05)
S− = significantly less than E0028 (LSD 0.05)

TABLE 13

Single year data from MSU Wheat State Performance Trials (years included are indicated).

| Name | Stripe Rust Score (0-9) 2007 | Barley Yellow Dwarf Virus Score (0-9) 2007 | Wheat Spindle Streak Mosaic Virus Score (0-9) 2006 HARVEST | Winter Kill (Injury) Score (0-9) 2005 |
|---|---|---|---|---|
| MSU Line E0028 | 1.7 | 4.0 | 2.0 | 0.8 |
| MSU D8006W | 0.7 | 0.6 S− | 1.0 | 1.1 |
| Crystal (MSU E0027) | 5.0 S+ | 1.0 S− | 2.0 | 0.6 |
| Jewel (MSU E1007W) | 2.0 | 0.6 S− | 1.0 | 1.2 |
| Aubrey | 0.3 | 1.8 S− | 3.0 | 1.7 |
| Pioneer Brand 25W41 | 0.0 S− | 1.9 S− | 1.0 | 1.9 |
| Caledonia | 1.0 | 2.3 S− | 2.0 | 4.5 S+ |
| Trial Mean | 0.9 | 2.1 | 3.3 | 1.8 |
| LSD (0.05) | 1.5 | 1.7 | 3.1 | 1.6 |
| CV (%) | 103.0 | 56.2 | 45.3 | 55.5 |

S+ = significantly more than E0028 (LSD 0.05)
S− = significantly less than E0028 (LSD 0.05)

The following characteristics of variety E0028 are ascertained by breeder evaluation of the data presented in Tables 1-13. Variety E0028 performs well in terms of yield and flour yield. It also performs acceptably for milling and baking qualities. It is not significantly different from average for multiyear data for other traits, including flowering time, lodging, black point, leaf rust, leaf blotch, and powdery mildew.

The deoxynivalenol (DON) levels of E0028 are higher than average, though not significantly different from other wheat varieties, nor are they significantly different from Caledonia, which is widely grown in Michigan. With respect to the DON levels, there are white wheat varieties in commercial production with significantly lower levels of DON. Exceeding acceptable DON levels at the elevator may result in the inability of the farmer to sell the grain. In some cases, growers may be penalized for higher levels of DON, up to a point, and after this point the elevator will not purchase the grain. Shown in Table 14 below, are the U.S. federal advisory limits for DON for various final products.

TABLE 14

U.S. Federal Advisory Limits for Deoxynivalenol (DON) in parts per million (ppm).

| DON ppm | Type of Products |
|---|---|
| 1 | Finished wheat products for human consumption. |
| 5 | Grain and grain byproducts destined for swine and other animal species (except cattle and chickens); not to exceed 20 percent of the diet for swine, and not to exceed 40 percent for other animal species. |
| 10 | Grain and grain byproducts for ruminating beef and feedlot cattle older. |

Varying levels of controlling *Fusarium* Head Blight (FHB) and deoxynivalenol (DON) levels may be possible through fungicide applications. However, consideration should also be given to the fact that years of data show red wheat varieties in Michigan, in general, have lower DON levels than white wheat varieties in Michigan. It is not yet known if this is a genetic factor in red versus white wheat. It should be noted that the DON levels of the red wheat varieties are factored into the mean of the State Performance Trial (the mean data reported here), thereby decreasing the overall wheat average relative to the score for E0028. FHB visual symptoms (% incidence, % severity, and % FHB Index) are also high in E0028, but they are not significantly different from the average performance of varieties in the State Performance Trial when multiyear data are considered. *Fusarium* damaged kernels, a trait sometimes considered by breeding programs, has not been investigated with respect to the performance of E0028 for this characteristic.

Test weight of E0028 is lower than average, and although the data do not provide a definitive statistical comparison, it appears that earlier harvest would likely not significantly increase the test weight. However, despite the test weight being low, it is not significantly less than the Caledonia variety and two other soft white wheat varieties from Michigan State University.

Experimental details for the Michigan State Wheat Performance Trials and data collection for MSU Line E0028 include the following aspects. Wheat plots are 12 feet long and have 6 rows at 7.5" row spacing. The trial is designed and executed as a four replication alpha-lattice (14 blocks of 5 plots each) at all sites except the scab screening nursery. All seed is treated, but the chemicals and rates of use vary according to the preferences of the originating organization. Seeding rates per linear foot of row are standardized to the rate that would equate with a stand of 2.0 million seeds per acre in a solid stand planted in 7.5" rows. Fall fertilizer application varies with cooperator practice. Spring nitrogen is applied as urea (90 lbs/acre actual N) at green-up. No foliar fungicides are applied at any site. Weeds are chemically controlled as needed. All plots at a site are harvested on a single day. Yield is calculated using the entire area of the plot including the wheel tracks between plots. This approach tends to underestimate yield. Data reported as scores is based on a 0-9 scale, where 0 is the best possible score. Yield, test weight, and grain moisture data are acquired electronically on the plot combine at the time of harvest. Yield data is standardized to 13% moisture.

Data are collected for flowering date, leaf rust, stripe rust, plant height, powdery mildew, barley yellow dwarf virus, and leaf blotch. The flowering date indicates the average number of days past January 1st that a given entry reached the point where one-half of its heads are flowering. Leaf rust, stripe rust, powdery mildew, barley yellow dwarf virus, and leaf blotch scores are recorded as "0=no visual symptoms of disease present". Plant height is reported as the distance in inches from the ground to the tip of average heads in a plot. Leaf and stripe rust scores are based on infection observations of primarily the flag leaf. Powdery mildew scores are based on observations of the entire plant including the flag leaf. Barley Yellow Dwarf Virus (BYDV) is transmitted through aphids and is enhanced with cool temperatures and rain. Barley Yellow Dwarf scores may not be reflective of actual resistance because some cultivars may have seed treated with insecticides prior to planting. Early infestations (fall) of aphids may be controlled using certain seed treatments, masking BYDV susceptibility. The causal organism(s) of the leaf blotching are not identified, but are likely a combination of *Stagonospora tritici*, (formerly known as *Septoria tritici*), and *S. nordorum*.

Data collection for wheat spindle streak mosaic virus, sprouting, and *Fusarium* head blight include the following details. Wheat spindle streak mosaic virus is transmitted into wheat roots via a soil borne fungus called *Polymyxa graminis*. Infections take place during cool, wet periods. The optimal temperature for symptoms to appear is between 48° F. and 55° F. Sprouting data is based on a greenhouse evaluation of 5 heads. Heads are collected within four hours of harvest and dried for approximately seven days. Scores are taken after the heads are subjected to near-continuous misting for three to four days. A score of zero indicates that sprouting was not present. A score of 9 indicates many shoots and roots observed in the heads during scoring.

Data on *Fusarium* head blight (scab) are obtained from the Ingham misted/inoculated scab screening nursery. The Ingham scab nursery is inoculated (from lab-produced infected grain spread onto the field), and artificial misting is employed throughout the entire flowering period. Each wheat head (i.e., 'spike') is comprised of roughly 14-22 "spikelets," which bear the developing seed. Spikelets that prematurely die because of scab infection are called "scabby" spikelets. Field symptom data are based on: 1) the percent of spikes showing any scabby spikelets; 2) the percent of scabby spikelets within infected spikes; and 3) the percent of scabby spikelets considering all spikes (scab index). The scab index is a measure of the extent of damage to entire plots due to scab infection, and generally relates to the effect of scab on yield. Deoxynivalenol (DON) data is from harvested grain in the inoculated, mist irrigated, scab screening nursery. DON data is presented in parts per million (ppm). The grain was analyzed at Michigan State University using an ELISA kit (Veratox® for DON5/5, Product #8331) from Neogen® (Lansing, Mich.) in 2005, and at the University of Minnesota using gas chromatography mass spectrometry from 2006-2008 (Fuentes, R. G., Mickelson, H. R., Busch, R. H., Dill-Macky, R., Evans, C. K., Thompson, W. G., Wiersma, J. V., Xie, W., Dong, Y., and Anderson, J. A. 2005, Resource Allocation and Cultivar Stability in Breeding for *Fusarium* Head Blight Resistance in Spring Wheat. Crop Sci. 45: 1965-1972).

Black point is the discoloration of the embryo (germ) end and surrounding areas of the wheat kernel. The embryo tip shows a black to brown discoloration that may extend into the crease of the kernel. Visual observations consist of 500 seed lots from one rep at each of two locations observed. Data includes the average percent of kernels discolored. The milling and baking quality data are determined by the USDA Eastern Soft Wheat Quality Laboratory in Wooster, Ohio. Flour yield is the ratio of the weight of extractable flour to the weight of milled grain, expressed as a percentage. Lactic Acid Retention is used by some soft wheat processors as a measure of protein strength. Higher "softness equivalent percents" indicate a softer grained wheat.

Traits measured in replicated trials conducted from 2001 onward in Michigan included grain yield (kg ha$^{-1}$, adjusted to 13% moisture), test weight (kg hL$^{-1}$), flowering date (days past January 1), plant height (cm) and black point (percent observed post-harvest). Additionally, the following traits were observed and recorded on a 0 to 9 scale, where 0 was desirable; plant lodging, winter injury, leaf rust, stripe rust (*Puccinia striiformis* Westend.), powdery mildew, leaf blotch Barley yellow dwarf virus (BYDV), and Wheat spindle streak mosaic virus (WSSMV).

In each year that E0028 was included in a Michigan yield trial (2001-2008), it was also included in MSU's artificially inoculated and overhead irrigated FHB screening nursery. Plot sizes, inoculation methods and number of replications evaluated in the FHB nursery varied by year. The FHB data from the MSPT reported here (2006-2008) were from trials inoculated with wheat grain, plus barley grain in 2007, colonized with *Fusarium graminearum* lineage 7. Inoculum was spread in the trial at a rate of 27 kg ha$_{-1}$ to 33.6 kg ha$_{-1}$ (rate varied by year) per inoculation date. Inoculum was applied twice, approximately two weeks apart, to the entire trial. The first application date was applied when it was predicted that antithesis would approximately two to three weeks later. Genotypes were planted as 1 row plots, 4 feet long in 2006 and 5 feet long in 2007 and 2008. Overhead (mist) irrigation was employed on an hourly schedule following the application of the inoculum and through the completion of flowering. Data on both incidence and severity were collected and used to calculate the FHB index (FHB index=incidence*severity/100) to represent the percentage of overall FHB infection in a plot. DON mycotoxin data were also collected from samples harvested from the FHB nursery field trials. DON from the 2006 through 2008 harvests was quantified in parts per million using gas chromatography mass spectrometry at the University of Minnesota (Fuentes et al., 2005, Resource Allocation and Cultivar Stability in Breeding for *Fusarium* Head Blight Resistance in Spring Wheat. Crop Sci. 45: 1965-1972).

E0028 was also evaluated at additional sites through cooperative regional tests, including the 2007 Uniform Eastern Soft Red Winter Wheat Nursery (UESRWWN, coordinated by USDA-ARS, 59 cooperators in 22 US states) and the 2007 and 2008 OPT (10 sites, Ontario, Canada). Trait data collected in the UESRWWN included a wide range of data pertaining to agronomics, disease and pest resistance, quality, and molecular marker data for a select group of loci. Data collected in the OPT also included agronomic traits and disease resistance.

From 2005 through 2008, a grain sample of 400 to 500 g of each cultivar entered in the MSPT was obtained from a 1:1 mix of two yield-trial location harvests in Michigan. Sites used for the mixture each year were selected for absence of pre-harvest sprouting and a minimum of other grain defects such as *Fusarium* damaged kernels. Samples from yield trial sites in the following counties were mixed as follows for each year: Saginaw and Midland Counties in 2005, 2007 and 2008; Saginaw and Lenawee Counties in 2006. Prior to milling, samples were aspirated to remove broken, shrunken, and diseased kernels. Whole grain moisture determination used low speed corrugated rolls to coarsely break grain and then the oven drying method (Method 44-15A) of the American Association of Cereal Chemistry (AACC Approved Methods, 10$^{th}$ ed., 2000), to measure grain moisture content. Samples were then tempered to 15% grain moisture. Tempered grain samples were milled after 48 hours to allow for equal water distribution throughout the kernel. Samples were milled using modifications to AACC Method 26-50 as described by Finney and Andrews (1986) Revised microtesting for soft wheat quality evaluation. Cereal Chem. 63:177-182. Milling of 200 g samples was conducted on a modified Quadrumat Junior flour mill in a controlled temperature and humidity room (19 to 21° C. and RH 55% to 60%). Product from the mill was recovered for sifting on a Great Western Sifter Box to separate mill product into bran (particles remaining above a 470 μm mesh), flour mids (between 470 and 180 μm mesh) and fine flour (particles passing through a 180 μm mesh). Flour mids were further processed through reduction milling with smooth rolls on a second Quadrumat Junior mill and sieved on a Great Western Sifter box using a 213 μm mesh screen to produce baking quality flour. Softness equivalent (SE) was calculated as fine flour (flour passing through the 180 μm mesh screen) recovered from the first milling process expressed as a percent of the total weight of milled grain. Softness equivalent is an estimator of break flour yield from a long-flow multi-stream flour mill. Flour yield was corrected based on softness equivalent to predict flour yield on the long-flow experimental Allis Chalmers mill at the Soft Wheat Quality Laboratory (Gaines et. al 2000, Developing Agreement between Very Short Flow and Longer Flow Mills. Cereal Chemistry 77: 187-192).

Flour quality was analyzed using the solvent retention capacity (SRC) test, AACC Method 56-11 (AACC 2000), with the following modifications. Flour sample size for the SRC analysis was 1 g, suspended in 5 g of solvent. Disposable glass centrifuge tubes were used for the analysis. Suspension of the flour in the solvent used a vortex mixer for 20 s at 5 min intervals for 15 min. All other protocols conformed to the AACC standard method. Lactic acid SRC was used for all four years of the evaluations; all other solvents were used for flour analysis only in 2007 and 2008. Initial flour moistures were determined by oven method (AACC Method 44-16). Flour protein was determined using Near Infra-Red Reflectance (SpectraStar 2400, Unity Scientific, Columbia Md.) calibrated by combustion analysis (rapidN III, Elementar Instruments, Cambridge UK) of a subset of samples each year. Baking evaluation for soft wheat quality used the micro sugar-snap cookie method (AACC Method 10-52). The diameters across two cookies were measured at four different positions of the cookies, and the four measurements were averaged and reported as the sum of two cookie diameters. A visual assessment of topgrain cracking of the cookie surface also was scored using a 0 to 9 scale by comparing to photographs of standard cookies. Greater amounts of cracking of the cookie surface indicate greater collapse of the cookie at the end of the baking sequence and are generally preferred for soft wheat quality. Greater score values indicate greater amounts of surface cracking.

MSU yield trials (PYT, AYT, MSPT) and associated FHB screening trials were planted in replicated designs, either alpha-lattice designs or randomized complete block designs. Data from these trials were analyzed by residual maximum likelihood (Patterson and Thompson, 1972, "Recovery of inter-block information when block sizes are unequal" Biometrika 58: 545-554) in the program "REML" (Thompson et al., 1982, REML a Program for the Analysis of Non Orthogonal Data by Restricted Maximum Likelihood, COMPSTAT: Proceedings in Computational Statistics. Physica Verlag, Wien, 231-232), which not only takes into account locations and replications, but neighboring plots as well. The coefficients of variations and the Least Significant Differences (LSDs) using a P-value of 0.05 were also determined. For quality analyses, an F-test for significance of genotypes used an analysis of variance in SAS PROC GLM (SAS version 9.0, 2003) assuming that genotypes were fixed effects and years were random effects and that the error term for genotypes was the interaction of genotypes and years. When possible, trait data are presented as averages across years (three-year averages except for yield, test weight and quality, for which four year averages are presented), though not all traits were assessed in all years.

The majority of data presented below were collected on the MSPT. For ease of comparisons between varieties, only data of entries present in all years from 2005 to 2008 are included in Tables 15 through 19. Trial means, LSDs and CVs reported in Tables 15 to 18 were determined using data of the entire trial each year, of which the reported cultivars here are only a subset.

In MSPT trials, the three year average of the flowering date of E0028 (152.3 Julian Days Flowering) is the same as the trial mean (Table 15). In addition, lodging (2.8) and winter injury (0.8) are not significantly different from the two year and one year trial means for these traits (89 cm, 3.5, 1.8, respectively, $LSD_{p<0.05}$ for lodging and winter injury=1.8 and 1.6, respectively).

TABLE 15

Agronomic traits of E0028 (i.e., "Ambassador") in comparison with other wheat varieties included in the MSPT. The scale used for evaluation of each trait is shown in parenthesis after the name of the trait.

| Cultivar | Cultivar Reference | Class | Flowering Date, days past 1 January 3 YR† 06-08‡ | Height cm 3 YR 06-08 | Lodging 0-9 2 YR 05-06 | Winter Injury 0-9 1 YR 2005 |
|---|---|---|---|---|---|---|
| Ambassador§ | This publication | SWW | 152.3 | 90.5 | 2.8 | 0.8 |
| 25R47 | PVP¶ 200200232, 2003 | SRW | 152.1 | 83.3 | 3.3 | 1.3 |
| 25W41 | PVP 200300328, 2004 | SWW | 152.4 | 86.0 | 3.9 | 1.9 |
| AC Mountain | NR#, Agriculture Canada | SWW | 152.9 | 99.8 | 3.9 | 0.8 |
| Aubrey | Private Company†† | SWW | 151.7 | 90.0 | 2.1 | 1.7 |
| Bravo | PVP 200000326, 2002 | SRW | 150.9 | 94.8 | 3.0 | 1.1 |
| Caledonia | Sorrells et al., 2004 | SWW | 152.7 | 86.0 | 2.4 | 4.5 |
| Coral | NR, MSU | SWW | 153.6 | 95.3 | 3.8 | 1.1 |
| Crystal | PVP 200800367 | SWW | 153.3 | 88.0 | 2.7 | 0.6 |
| D6234 | PVP 200300259, 2004 | SWW | 153.1 | 93.0 | 3.6 | 2.2 |
| D8006 | PVP 200500308, 2006 | SWW | 152.0 | 90.8 | 4.0 | 1.1 |
| DF101 | Private Company | SRW | 151.2 | 87.5 | 3.2 | 1.0 |
| Emmit | NR, Hyland Seeds | SRW | 153.0 | 90.3 | 2.9 | na‡‡ |
| Hopewell | Campbell et al., 2001 | SRW | 152.4 | 91.8 | 2.0 | 1.3 |
| Jewel | PVP 200700408, 2008 | SWW | 152.4 | 91.0 | 2.5 | 1.2 |
| McCormick | Griffey et al., 2005a | SRW | 151.6 | 78.5 | 5.1 | 2.3 |
| MCIA Oasis | NR, Ohio State University | SRW | 152.2 | 98.5 | 3.1 | na |
| R045 | Private Company | SRW | 151.9 | 87.0 | 4.5 | 0.8 |
| R055 | Private Company | SRW | 152.0 | 84.8 | 2.3 | 1.8 |
| Red Amber | NR, MSU | SRW | 152.9 | 93.3 | 3.6 | 2.0 |
| Red Ruby | PVP 200700409 | SRW | 153.1 | 89.3 | 2.5 | 1.1 |
| Roane | Griffey et al., 2001 | SRW | 151.6 | 83.0 | 3.9 | 1.1 |
| Tribute | Griffey et al., 2005b | SRW | 151.2 | 82.8 | 4.2 | 1.6 |
| Trial Mean | | | 152.3 | 89.0 | 3.5 | 1.8 |
| $LSD_{p<0.05}$ | | | 0.7 | 3.5 | 1.8 | 1.6 |
| CV (%) | | | 0.8 | 2.4 | 25.5 | 55.5 |

†The number of years averaged is shown by "YR", with the details of the years included below.
‡Years that are averaged are indicated by the last two digits of the first and last years of the range of years included (e.g. 06-08 = average of 2006, 2007 and 2008).
§Ambassador (i.e., E0028) listed first, with other entries sorted by name.
¶Plant Variety Protection (PVP) number given
NR = Not Registered. Culativars listed as NR have known origin, and these origins are indicated.
††Cultivars listed as "Private Company" were provided by private companies without information of their origin.
‡‡na, not available The four-year (2005 through 2008) MSPT average yield of E0028 (6160 kg ha$^{-1}$) was significantly greater than the four-year trial mean (5931 kg ha$^{-1}$, $LSD_{p<0.05}$=242) (Table 16). However, when examining each year separately, the yield of E0028 was only significantly greater than the trial means in 2006 and 2007. Of the varieties presented in Table 16, only '25R47' was consistently higher yielding than E0028 across in each of the four years, though this difference was only significant in 2005 (25R47, 6005 kg ha$^{-1}$; E0028 5528 kg ha$^{-1}$; $LSD_{p<0.05}$=289 kg ha$^{-1}$), and the four year average yield (6348 kg ha$^{-1}$) was not significantly different. In comparison with 'Calcdonia', the most widely grown soft white wheat in Michigan, E0028's yield was consistently greater in each of the four years, and was significantly greater for the four-year average (Calcdonia=5723 kg ha$^{-1}$). Regarding test weight, E0028's fouryear average (74.1 kg hL$^{-1}$) was significantly less than the trial mean (76.1 kg hL$^{-1}$, $LSD_{p<0.05=0.9}$) as well as all other cultivars included in Table 16 with the exceptions of 'Crystal' (74.6 kg hL$^{-1}$) and 'AC Mountain' (74.6 kg hL$^{-1}$).

TABLE 16

Yield (kg ha$^{-1}$) adjusted to 13% moisture, and test weight kg hL$^{-1}$) for MSPT entries. Four year averages for yield and test weight are shown, in addition to the yield of each individual year.

| | | Yield kg ha$^{-1}$ (Adjusted to 13% Moisture) | | | | | Test weight kg hL$^{-1}$ |
|---|---|---|---|---|---|---|---|
| | | | | 1 YR | | | |
| Cultivar | Class | 4 YR† 05-08‡ | 2008 | 2007 | 2006 | 2005 | 4 YR 05-08 |
| 25R47§ | SRW | 6348 | 6254 | 6395 | 6745 | 6005 | 75.3 |
| Ambassador | SWW | 6160 | 6100 | 6322 | 6691 | 5528 | 74.1 |
| Red Ruby | SRW | 6160 | 6147 | 6234 | 6631 | 5629 | 77.2 |
| MCIA Oasis | SRW | 6106 | 6066 | 6335 | 6530 | 5501 | 75.3 |
| Hopewell | SRW | 6100 | 6133 | 6221 | 6328 | 5710 | 75.9 |
| D8006 | SWW | 6100 | 6026 | 6362 | 6584 | 5434 | 75.0 |
| Crystal | SWW | 6093 | 6032 | 6274 | 6530 | 5528 | 74.6 |

TABLE 16-continued

Yield (kg ha$^{-1}$) adjusted to 13% moisture, and test weight kg hL$^{-1}$) for MSPT entries. Four year averages for yield and test weight are shown, in addition to the yield of each individual year.

| | | Yield kg ha$^{-1}$ (Adjusted to 13% Moisture) | | | | | Test weight kg hL$^{-1}$ |
|---|---|---|---|---|---|---|---|
| | | | | 1 YR | | | |
| Cultivar | Class | 4 YR† 05-08‡ | 2008 | 2007 | 2006 | 2005 | 4 YR 05-08 |
| R045 | SRW | 6079 | 6348 | 6328 | 6322 | 5319 | 76.4 |
| Emmit | SRW | 6053 | 6026 | 6079 | 6449 | 5649 | 76.1 |
| R055 | SRW | 6012 | 5609 | 6120 | 6631 | 5696 | 76.3 |
| Red Amber | SRW | 5979 | 5945 | 6160 | 6409 | 5393 | 75.9 |
| DF101 | SRW | 5972 | 5844 | 6032 | 6369 | 5642 | 77.5 |
| Coral | SWW | 5965 | 5864 | 6046 | 6422 | 5521 | 75.9 |
| Jewel | SWW | 5952 | 5891 | 6140 | 6362 | 5420 | 76.2 |
| Tribute | SRW | 5898 | 5528 | 6248 | 6322 | 5488 | 78.8 |
| 25W41 | SWW | 5857 | 5878 | 5938 | 6281 | 5319 | 76.6 |
| D6234 | SWW | 5824 | 5958 | 5844 | 6100 | 5400 | 76.6 |
| AC Mountain | SWW | 5817 | 5831 | 5750 | 6315 | 5367 | 74.6 |
| Aubrey | SWW | 5804 | 5810 | 5911 | 5905 | 5595 | 77.2 |
| Caledonia | SWW | 5723 | 5575 | 5588 | 6375 | 5353 | 75.1 |
| Bravo | SRW | 5696 | 5723 | 5555 | 5925 | 5568 | 76.8 |
| Roane | SRW | 5521 | 5548 | 5676 | 5676 | 5178 | 78.4 |
| McCormick | SRW | 5266 | 5192 | 5118 | 5535 | 5212 | 77.7 |
| Trial Mean | | 5931 | 5871 | 5898 | 6113 | 5380 | 76.2 |
| LSD$_{p<0.05}$ | | 242 | 309 | 276 | 471 | 289 | 0.9 |
| CV (%) | | 2.9 | 3.8 | 4.1 | 6.2 | 4.7 | 0.8 |

†The number of years averaged is shown by "YR", with the details of the years included below.
‡Years that are averaged are indicated by the last two digits of the first and last years of the range of years included (e.g. 06-08 = average of 2006, 2007 and 2008).
§Entries are sorted by highest 4 year average yield.

Data from the UESRWWN [www.ars.usda.gov/main/docs.htm?docid=2925] and the OPT [gocereals.ca/] further supported the yield test weight performance that was observed in Michigan. For the UESRWWN yield data, which included forty-four entries evaluated at twenty-two sites, E0028 had an average yield of 5248 kg ha$^{-1}$, which was greater than the trial mean (4791 kg ha$^{-1}$) as well a the four checks 'Foster' (4529 kg ha$^{-1}$), Patton'(4629 kg ha$^{-1}$), 'Roane' (5140 kg ha$^{-1}$) and INW0411'(4603 kg ha$^{-1}$). For test weight, which was evaluated at twenty-one sites, E0028 had an average test weight of 72.9 kg hL$^{-1}$, which was lower than the mean (75.0 kg hL$^{-1}$), as well as the four checks (Foster, 74.8 kg h$^{-1}$; Patton, 74.3 kg hL$^{-1}$; Roane, 76.6 kg hL$^{-1}$; INW0411, 73.8 kg h$^{-1}$). The OPT data are reported according to Areas, which are defined according to climatic conditions. Area 1 is the southwest portion of Ontario, which is the warmest, Area II is less warm and has more snowfall, and Area III is eastern Ontario, which has more ice accumulation. Among eight soft white winter wheat cultivars, E0028 showed the highest yield (5622 kg ha$^{-1}$), on a two-year average for Areas I and II combined (mean=4354 kg ha$^{-1}$, 12 sites included), and Area III alone for a two-year average (E0028 yield=5622 kg ha$^{-1}$, mean=5406 kg ha$^{-1}$, 6 sites included). E0028's test weight, however, was the lowest for its class in each of Areas I (73.3 kg 0.5 L$^{-1}$), II and III. Additional data can be viewed at the 2008 winter wheat report at http://gocereals.ca/.

E0028 has been characterized for disease and insect resistance in Michigan and through cooperative regional evaluations (Tables 17 and 18). Considering the three-year averages (2006 through 2008) of FHB incidence, severity and index, only the percent FHB severity (55.9%) was significantly greater than the three-year average of the MSPT (41.0%, LSD$_{p<0.05=14.4}$) (Table 17). Although E0028's FHB index (28.4%) was not significantly different from the three-year average (26.1%, LSD$_{p<0.05}$=15.6), amongst the other cultivars in Table 17 it is only less than Calcdonia (42.0%), the most widely grown soft white wheat in Michigan. FHB incidence for E0028 (69.9%) was not significantly different from the three year average of the MSPT (62.3%, LSD$_{p<0.05}$=16.7). Knott et al., (2008, Comparison of selection methods for the development of white-seeded lines from red x white soft winter wheat crosses. Crop Sci 48: 1807-1816) showed that although visual symptoms of red vs. white grained wheat are not significantly different, the associated mycotoxin accumulation in white wheat is higher than red wheat. In comparison with other white wheat cultivars included in the MSPTs, the three-year average of E0028 for DON (10.0 ppm) is higher than all other cultivars listed in table 17 with the exception of Crystal (10.4 ppm), and is significantly higher than 'Aubrey' (4.1 ppm, LSD$_{p<0.05}$=5.6).

TABLE 17

Fusarium head blight (FHB) disease symptoms and deoxynivalenol (DON) mycotoxin accumulation shown in parts per million (ppm) for MSPT entries.

| Cultivar | Class | Incidence % of spikes | Severity % within infected spikes | Index % overall infection | DON ppm† |
|---|---|---|---|---|---|
| | | | 3 YR‡ 06-08§ | | |
| Ambassador¶ | SWW | 69.9 | 55.9 | 40.0 | 10.0 |
| 25R47 | SRW | 71.9 | 39.2 | 28.4 | 4.6 |
| 25W41 | SWW | 66.5 | 38.3 | 25.4 | 7.3 |
| AC Mountain | SWW | 52.1 | 50.8 | 26.8 | 4.9 |
| Aubrey | SWW | 63.5 | 35.0 | 21.8 | 4.1 |
| Bravo | SRW | 69.9 | 39.8 | 28.6 | 4.0 |
| Caledonia | SWW | 66.9 | 59.9 | 42.0 | 8.3 |
| Coral | SWW | 51.6 | 36.8 | 20.8 | 5.3 |
| Crystal | SWW | 59.2 | 51.8 | 30.2 | 10.4 |
| D6234 | SWW | 67.0 | 51.0 | 32.3 | 6.0 |
| D8006 | SWW | 72.3 | 51.0 | 37.8 | 7.9 |

TABLE 17-continued

*Fusarium* head blight (FHB) disease symptoms and deoxynivalenol (DON) mycotoxin accumulation shown in parts per million (ppm) for MSPT entries.

| Cultivar | Class | Incidence % of spikes | Severity % within infected spikes | Index % overall infection | DON ppm† |
|---|---|---|---|---|---|
| | | 3 YR‡ 06-08§ | | | |
| DF101 | SRW | 68.9 | 31.8 | 21.2 | 3.8 |
| Emmit | SRW | 51.5 | 42.1 | 21.4 | 3.6 |
| Hopewell | SRW | 71.6 | 46.1 | 33.8 | 5.3 |
| Jewel | SWW | 74.9 | 46.1 | 34.6 | 9.6 |
| McCormick | SRW | 57.6 | 28.5 | 14.3 | 2.5 |
| MCIA Oasis | SRW | 60.9 | 42.8 | 26.6 | 4.2 |
| R045 | SRW | 61.8 | 35.6 | 22.0 | 4.9 |
| R055 | SRW | 60.4 | 38.3 | 22.6 | 3.5 |
| Red Amber | SRW | 60.9 | 53.1 | 32.3 | 6.5 |
| Red Ruby | SRW | 63.0 | 43.3 | 31.0 | 6.3 |
| Roane | SRW | 61.0 | 32.4 | 19.3 | 2.6 |
| Tribute | SRW | 50.7 | 30.7 | 15.1 | 3.6 |
| Trial Mean | | 62.3 | 41.0 | 26.1 | 3.8 |
| LSD$_{p<0.05}$ | | 16.7 | 14.4 | 15.6 | 5.6 |
| CV (%) | | 16.3 | 21.5 | 36.6 | 42.0 |

†ppm = parts per million
‡The number of years averaged is shown by "YR", with the details of the years included below.
§Years that are averaged are indicated by the last two digits of the first and last years of the range of years included (e.g. 06-08 = average of 2006, 2007 and 2008).
¶Ambassador (i.e. E0028) listed first, other entries sorted by name.

E0028's responses to additional diseases are shown in Table 18. E0028 is susceptible to leaf rust. Although E0028's susceptibility (5.2) to leaf rust was not significantly worse than the three-year trial mean (3.8, LSD$_{p<0.05}$=1.5), only 'McCormick' (6.7) and 'Bravo' (5.8) had higher leaf rust values. The susceptibility of 'Hopewell' (5.2), the most widely grown soft red wheat in Michigan, was equivalent to E0028. For powdery mildew, E0028 (2.8) was not significantly different from the trial mean (2.7, LSD$_{p<0.05}$=1.1). However, BYDV data from 2007 show that E0028 (4.0) is significantly worse than the trial mean (2.1, LSD$_{p<0.05}$=1.7), being surpassed only by 'Emmit' (4.5) for susceptibility. In 2006, WSSMV was present and rated in Michigan, and E0028 was more resistant (2.9) than the trial mean (3.3), being significantly less susceptible than Roane, Emmit and 'DF101' (9.0, 6.0, and 7.0, respectively, LSD$_{p<0.05}$=3.1). For post-harvest evaluations of percent black point, E0028 (11.7) was more resistant than the trial mean (17.6), and was significantly better than many other varieties (LSD$_{p<0.05}$=15.2).

Stem and leaf rust were evaluated with multiple races through the UESRWWN at the USDA Cereal Disease Rust Laboratory, MN. For stem rust, seedling reactions of E0028 to *Puccinia graminis* f. sp. *tritici* (*P. graminis* Pers.:Pers. f. sp. *tritici* Eriks. & E. Henn.) U.S. races QFCS, QTHJ, RCRS, RKQQ, TPMK, TTTT, TTKS were susceptible, though there was a low infection frequency for TPMK and TTTT, and mostly zero infection for RKQQ (heterogeneous reaction). Based on reactions to leaf rust races BBBD, MFPS, MJBJ,

TABLE 18

Disease response to Leaf and Stripe Rust, Powdery Mildew (PM), Barley Yellow Dwarf Virus (BYDV) and Wheat Spindle Streak Mosaic Virus (WSSMV) for MSPT entries. Quantification of the % of black point observed on harvested grain.

| Cultivar | Class | Leaf Rust 3 YR‡ 06-08§ | Stripe Rust 1 YR 2007 | PM 0-9 3 YR 06-08 | BYDV 1 YR 2007 | WSSMV 1 YR 2006 | Black Point % 3 YR 05-07 |
|---|---|---|---|---|---|---|---|
| Ambassador | SWW | 5.2 | 1.7 | 2.8 | 4.0 | 2 | 11.7 |
| 25R47 | SRW | 2.9 | 0 | 3.7 | 0.6 | 3 | 21.7 |
| 25W41 | SWW | 3.3 | 0 | 4.6 | 1.9 | 1 | 37.5 |
| AC Mountain | SWW | 4.9 | 1.0 | 3.3 | 2.9 | 2 | 18.3 |
| Aubrey | SWW | 4.5 | 0.3 | 1.6 | 1.8 | 3 | 10.0 |
| Bravo | SRW | 5.8 | 0 | 5.0 | 3.2 | 2 | 11.3 |
| Caledonia | SWW | 5.1 | 1.0 | 3.8 | 2.3 | 2 | 12.1 |
| Coral | SWW | 3.7 | 3.7 | 4.4 | 2.1 | 1 | 14.5 |
| Crystal | SWW | 3.6 | 5.0 | 2.0 | 1.0 | 2 | 3.1 |
| D6234 | SWW | 3.3 | 3.3 | 2.7 | 0.7 | 1 | 40.2 |
| D8006 | SWW | 4.4 | 0.7 | 2.1 | 0.6 | 1 | 27.5 |
| DF101 | SRW | 3.5 | 0.3 | 1.2 | 2.2 | 7 | 12.5 |
| Emmit | SRW | 4.6 | 4.3 | 3.8 | 4.5 | 6 | 36.3 |
| Hopewell | SRW | 5.2 | 0 | 3.2 | 1.5 | 1 | 5.0 |
| Jewel | SWW | 4.0 | 2.0 | 3.5 | 0.6 | 1 | 8.4 |
| McCormick | SRW | 6.7 | 0 | 0.5 | 1.0 | 2 | 20.9 |
| MCIA Oasis | SRW | 0.8 | 0.7 | 1.5 | 2.9 | 1 | na§ |
| R045 | SRW | 3.2 | 3.0 | 3.4 | 1.1 | 3 | 34.3 |
| R055 | SRW | 3.5 | 0.7 | 2.6 | 1.1 | 4 | 34.2 |
| Red Amber | SRW | 3.3 | 0 | 1.3 | 1.0 | 2 | 20.0 |
| Red Ruby | SRW | 3.8 | 3.0 | 2.9 | 0.4 | 1 | 11.7 |
| Roane | SRW | 3.2 | 0.3 | 3.4 | 0.8 | 9 | 5.3 |
| Tribute | SRW | 0.2 | 2.7 | 0.3 | 1.6 | 4 | 31.3 |
| Trial Mean | | 3.8 | 0.9 | 2.7 | 2.1 | 3.3 | 17.6 |
| LSD$_{p<0.05}$ | | 1.5 | 1.5 | 1.1 | 1.7 | 3.1 | 15.2 |
| CV (%) | | 23.7 | 103 | 24.5 | 56.2 | 45.3 | 53 |

†The number of years averaged is shown by "YR", with the details of the years cluded below.
‡Years that are averaged are indicated by the last two digits of the first and last years of the range o years included (e.g. 06-08 = average of 2006, 2007 and 2008).
§na = not applicable MCRK, KFBJ, MHDS, TGBG, TNRJ, it is postulated that E0028 has gene Lr9 relating to disease resistance.

E0028 has good soft wheat quality for pastry products based on milling and flour measurements. Calcdonia was the most widely grown soft white winter wheat in the eastern U.S. at the time of E0028's release. It is well accepted in the industry as a cultivar with targeted soft white quality attributes. E0028 had greater flour yield than Calcdonia at similar levels of softness equivalent and flour protein concentration (Table 19). Based on four years of evaluations, E0028 and Calcdonia have similar sugar snap two-cookie mean diameters (18.86 and 18.65 cm, respectively, $LSD_{p<0.05}$=0.51). Top grain scores (0 to 9 scale, where 9 is desirable) for E0028 and Calcdonia also were similar (4.3 and 4.9, respectively, $LSD_{p<0.05}$=1.5). The solvent retention capacity profile for E0028 was not significantly different from Calcdonia for any of the four solvents evaluated (Table 19). E0028 also had favorable milling and baking quality by comparison to the standard public soft red winter cultivar, Hopewell. E0028 had significantly greater flour yield than Hopewell with similar softness equivalent. E0028 had a greater sugar-snap two-cookie diameter than Hopewell (18.86 and 18.33 cm, respectively, $LSD_{p<0.05}$=0.51). Overall water absorption as measured by the SRC method was less for E0028's flour than for Hopewell's flour (50.33 and 51.83 g 100 g$^{-1}$, respectively, $LSD_{p<0.05}$=1.39). This was reflected in the lower sodium carbonate SRC for E0028 than Hopewell (64.38 and 70.18 g 100 g$^{-1}$, respectively, $LSD_{p<0.05}$=2.85), which suggests that the E0028 flour samples have less damaged starch due to milling than do the Hopewell samples. Based on the lactic acid SRC, E0028 has less gluten strength than Hopewell. E0028 had a lactic acid SRC of 96.68 g 100 g$^{-1}$ and Hopewell 111.55 g 100 g$^{-1}$.

Analysis of E0028 in 2008 and 2009 by the USDA-ARS Regional Small Grains Genotyping Laboratory, Raleigh N.C., showed that E0028 has the overexpressing allele for Bx7oe, contributing towards gluten strength (Glu-B1al). However, since the other high molecular weight glutenins are weak, notably the Glu-D1a allele at the Glu-D1 locus, E0028 is only moderate for gluten strength compared with other eastern soft winter wheat genotypes.

TABLE 19

Milling and baking quality for E0028 soft white winter wheat, Michigan trials, 2005 to 2008†.

| Cultivar | Class | Flour yield | Softness equivalent g 100 g$^{-1}$ | Flour protein | Sugar-snap cookie Diameter‡ cm | Top grain score 0-9¶ | Water§ | Solvent retention capacity solvents Sodium carbonate§ | Sucrose§ g 100 g$^{-1}$ | Lactic acid |
|---|---|---|---|---|---|---|---|---|---|---|
| Ambassador | SWW | 73.1 | 58.1 | 7.61 | 18.86 | 4.3 | 50.33 | 64.36 | 84.53 | 87.25 |
| 25R47 | SRW | 72.6 | 62.6 | 7.36 | 19.14 | 5.1 | 50.55 | 65.25 | 84.71 | 95.43 |
| 25W41 | SWW | 70.4 | 62.3 | 7.47 | 18.74 | 4.8 | 52.70 | 67.83 | 88.85 | 89.49 |
| AC Mountain | SWW | 71.6 | 58.0 | 7.68 | 18.51 | 5.0 | 51.21 | 65.53 | 84.55 | 86.21 |
| Aubrey | SWW | 71.3 | 59.6 | 8.20 | 17.99 | 3.7 | 52.14 | 66.76 | 87.39 | 102.16 |
| Bravo | SRW | 70.4 | 54.8 | 8.37 | 18.30 | 3.8 | 52.18 | 67.23 | 90.25 | 89.36 |
| Caledonia | SWW | 72.1 | 58.4 | 7.91 | 18.65 | 4.9 | 50.58 | 65.80 | 83.69 | 96.95 |
| Coral | SWW | 72.0 | 59.2 | 7.66 | 18.73 | 4.8 | 50.13 | 65.09 | 84.25 | 95.10 |
| Crystal | SWW | 72.6 | 57.9 | 7.61 | 18.57 | 4.5 | 51.62 | 66.33 | 84.25 | 91.65 |
| D6234 | SWW | 70.1 | 55.3 | 8.09 | 18.37 | 4.2 | 52.71 | 68.50 | 84.70 | 78.46 |
| D8006 | SWW | 73.3 | 60.5 | 7.96 | 18.67 | 4.6 | 51.22 | 65.87 | 86.67 | 107.41 |
| DF101 | SRW | 68.9 | 50.8 | 8.56 | 17.68 | 4.3 | 54.19 | 68.03 | 94.40 | 113.42 |
| Emmit | SRW | 72.5 | 57.0 | 7.72 | 18.28 | 4.3 | 53.11 | 67.52 | 87.60 | 79.52 |
| Envoy# | SWW | 71.9 | 53.9 | 8.17 | 18.22 | 4.0 | 54.21 | 68.58 | 90.55 | 105.74 |
| Hopewell | SRW | 69.4 | 60.0 | 7.98 | 18.33 | 4.3 | 51.83 | 70.18 | 88.55 | 109.69 |
| Jewel | SWW | 71.5 | 56.6 | 7.89 | 17.97 | 4.2 | 53.32 | 70.10 | 90.35 | 101.17 |
| McCormick | SRW | 70.2 | 59.0 | 8.52 | 17.76 | 4.8 | 55.35 | 71.93 | 94.95 | 108.54 |
| MCIA Oasis | SRW | 72.1 | 58.1 | 7.85 | 18.69 | 4.8 | 51.12 | 65.48 | 85.80 | 100.75 |
| Pearl†† | SWW | 71.0 | 59.0 | 8.04 | 18.41 | 3.7 | 52.56 | 69.58 | 88.60 | 106.38 |
| R045 | SRW | 72.2 | 59.2 | 7.81 | 18.46 | 4.5 | 54.66 | 71.21 | 89.70 | 91.45 |
| R055 | SRW | 72.3 | 58.8 | 7.86 | 18.52 | 5.8 | 52.09 | 64.00 | 87.55 | 94.20 |
| Red Amber | SRW | 71.4 | 54.7 | 8.41 | 18.42 | 4.3 | 50.76 | 66.13 | 85.95 | 103.95 |
| Red Ruby | SRW | 71.0 | 60.9 | 7.69 | 18.56 | 4.3 | 51.89 | 68.24 | 89.75 | 103.61 |
| Roane | SRW | 68.5 | 58.0 | 8.06 | 17.46 | 3.0 | 56.26 | 73.16 | 98.70 | 107.52 |
| Tribute | SRW | 70.2 | 53.3 | 8.19 | 17.92 | 4.0 | 57.55 | 73.38 | 97.45 | 111.78 |
| Average | | 71.3 | 57.7 | 7.96 | 18.37 | 4.4 | 52.65 | 67.95 | 88.69 | 98.85 |
| $LSD_{p<0.05}$ | | 0.8 | 3.0 | 0.48 | 0.43 | 1.3 | 0.97 | 1.91 | 3.47 | 7.27 |
| F-test for Cultivar | | 24.9*** | 8.13*** | 3.89*** | 8.36*** | 1.58 | 16.44*** | 8.06*** | 5.94*** | 16.17*** |

*F-test of cultivar variances significant at the 95% CI when tested with cultivar x year variance as the denominator.
***F-test of cultivar variances significant at the 99.9% CI when tested with cultivar x year variance as the denominator.
†Trials produced in Michigan and evaluated by the USDA-ARS Soft Wheat Quality Laboratory.
‡Sum of two cookie diameters.
§Water, sucrose, and sodium carbonate SRC evaluations were only conducted in 2007 and 2008.
¶For the top grain score, 9 is desirable.
Envoy was included in the 2005 AYT, and the MSPT following. It was licensed exclusively from MSU in 2008.
††Although Pearl was included in the MSPT from 2005-2008, not all data was reported. Therefore, only the quality data is being reported for these years (PVP# 200300114, 2003).

The present technology further includes the following aspects with respect to MSU Line E0028.

Reproduction of the MSU Line E0028 can occur by tissue culture and regeneration. Tissue culture of various tissues of wheat and regeneration of plants therefrom are performed using well known and widely published methods. A review of various wheat tissue culture protocols can be found in Maheshwari et al. (1995), In vitro culture of wheat and genetic transformation: Retrospect and Prospect, Critical Reviews in Plant Science, 14:149-178. Thus, another aspect of the present technology is to provide cells or tissue, which upon growth and differentiation, produce wheat plants capable of having the physiological and morphological characteristics of MSU Line E0028.

As used herein, a wheat plant includes various portions of the wheat plant such as plant protoplasts, plant cell tissue cultures from which wheat plants can be regenerated, plant calli, plant clumps, and plant cells that are intact in plants or portions of plants, such as embryos, pollen, ovules, pericarp, seed, flowers, florets, heads, spikes, leaves, roots, root tips, anthers, and the like.

Molecular biological techniques allow the isolation and characterization of genetic elements with specific functions, such as those encoding specific protein products. The genome of plants can be engineered to contain and express foreign genetic elements, or additional, or modified versions of native or endogenous genetic elements, in order to alter the traits of a plant in a specific manner. Any DNA sequence, whether from a different species or from the same species, which is inserted into the genome by transformation, is referred to herein collectively as a transgene. Several methods for producing transgenic plants have been developed, and embodiments of the present technology relate to transformed versions of the MSU Line E0028.

Numerous methods for plant transformation exist, including biological and physical, plant transformation protocols. See, for example, Mild B L, Fobert P, Charest P J, Iyer V N, (1993) Procedures for introducing foreign DNA into plants, In: Glick B R, Thompson J E, eds., Methods in plant molecular biology and biotechnology, Boca Raton, USA: CRC Press, 67-88. In addition, expression vectors and in vitro culture methods for plant cell or tissue transformation and regeneration of plants are available. See, for example, Gruber M Y, Crosby W L (1993) Vectors for plant transformation, In BR Glick, J E Thompson, Eds., Methods in Plant Molecular Biology and Biotechnology, CRC Press, Baton Rouge, La., pp 89-119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

Various genetic elements can be introduced into the plant genome using transformation. These elements include but are not limited to genes; coding sequences; inducible, constitutive, and tissue specific promoters; enhancing sequences; and signal and targeting sequences.

A genetic trait, engineered into a wheat plant with transformation techniques, can be moved or crossed into another line using traditional breeding techniques that are well known in the plant breeding arts. For example, a backcrossing approach could be used to move a transgene from a transformed wheat plant to an elite wheat variety and the resulting progeny would comprise a transgene. As used herein, "crossing" can refer to a simple X by Y cross, or the process of backcrossing, depending on the context. The term "breeding cross" excludes the processes of selfing or sibbing.

With transgenic plants according to the present technology, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney G. and On G. A., The purification of avidin and its derivatives on 2-iminobiotin-6-aminohexyl-Sepharose 4B, Anal. Biochem. 114(1): 92-6 (1981).

According to one embodiment, the transgenic plant provided for commercial production of foreign protein is a wheat plant. In another embodiment, the biomass of interest is seed. A genetic map can be generated, primarily via conventional RFLP, PCR, and SSR analysis, which identifies the approximate chromosomal location of the integrated DNA molecule. For exemplary methodologies in this regard, see Glick B R, Thompson J E, editors, Methods in plant molecular biology and biotechnology, (CRC Press, Boca Raton, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present technology, agronomic genes can be expressed in transformed plants. More particularly, plants can be genetically engineered to express various phenotypes of agronomic interest. Through the transformation of wheat the expression of genes can be modulated to enhance disease resistance, insect resistance, herbicide resistance, water stress tolerance, and agronomic traits as well as grain quality traits. Transformation can also be used to insert DNA sequences which control or help control male-sterility. DNA sequences native to wheat as well as non-native DNA sequences can be transformed into wheat and used to modulate levels of native or non-native proteins. Anti-sense technology, RNA interference, various promoters, targeting sequences, enhancing sequences, and other DNA sequences can be inserted into the wheat genome for the purpose of modulating the expression of proteins. Exemplary genes implicated in this regard include, but are not limited to, those categorized below.

1. Genes that confer resistance to pests or disease include one or more of those described as follows in (A)-(V):

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266: 789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al., Cell 78: 1089 (1994) (*Arabidopsis* RSP2 gene for resistance to *Pseudomonas syringae*); McDowell & Woffenden, (2003) Trends Biotechnol. 21(4): 178-83 and Toyoda et al., (2002) Transgenic Res. 11(6):567-82. A plant resistant to a disease is one that is more resistant to a pathogen as compared to the wild type plant.

*Fusarium* head blight along with deoxynivalenol both produced by the pathogen *Fusarium graminearum* Schwabe have caused devastating losses in wheat production. Genes expressing proteins with antifungal action can be used as transgenes to prevent *Fusarium* head blight. Various classes of proteins have been identified. Examples include endochitinases, exochitinases, glucanases, thionins, thaumatin-like proteins, osmotins, ribosome inactivating proteins, flavoniods, lactoferricin. During infection with *Fusarium graminearum* deoxynivalenol (DON) is produced. There is evidence that production of deoxynivalenol increases the virulence of the disease. Genes with properties for detoxification of deoxynivalenol (Adam and Lemmens, In International Congress on Molecular Plant-Microbe Interactions, 1996; McCormick et al. Appl. Environ. Micro. 65:5252-5256, 1999) have been engineered for use in wheat. A synthetic peptide that competes with deoxynivalenol has been identified (Yuan et al., Appl. Environ. Micro. 65:3279-3286, 1999). Changing the ribosomes of the host so that they have reduced affinity for deoxynivalenol has also been used to reduce the virulence of the *Fusarium graminearum*.

Genes used to help reduce *Fusarium* head blight include but are not limited to Tri101(Fusarium), PDR5 (yeast), tlp-1 (oat), tlp-2(oat), leaftlp-1 (wheat), tlp (rice), tlp-4 (oat), endochitinase, exochitinase, glucanase (Fusarium), permatin (oat), seed hordothionin (barley), alpha-thionin (wheat), acid glucanase (alfalfa), chitinase (barley and rice), class beta II-1,3-glucanase (barley), PR5/tlp (*arabidopsis*), zeamatin (maize), type 1 RIP (barley), NPR1 (*arabidopsis*), lactoferrin (mammal), oxalyl-CoA-decarboxylase (bacterium), IAP (baculovirus), ced-9 (*C. elegans*), and glucanase (rice and barley) (Dahleen, L. S., Okubara, P. A. and A. E. Blechl (2001) Transgenic Approaches to Combat *Fusarium* Head Blight in Wheat and Barley, Crop Science 41:628-637).

(B) A gene conferring resistance to a pest, such as Hessian fly, wheat, stem soft fly, cereal leaf beetle, and/or green bug. For example the H9, H10, and H21 genes.

(C) A gene conferring resistance to disease, including wheat rusts, *Septoria tritici, Septoria nodorum*, powdery mildew, helminthosporium diseases, smuts, bunts, *fusarium* diseases, bacterial diseases, and viral diseases.

(D) A *Bacillus thuringiensis* protein, a derivative thereof or a synthetic polypeptide modeled thereon. See, for example, Geiser et al., Gene 48: 109 (1986), who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Nos. 40098, 67136, 31995 and 31998. Other examples of *Bacillus thuringiensis* transgenes being genetically engineered are given in the following patents and patent applications and hereby are incorporated by reference for this purpose: U.S. Pat. Nos. 5,188,960, Payne et al, issued Feb. 23, 1993; 5,689,052, Brown et al, issued Nov. 18, 1997; 5,880,275, Fischhoff et al., issued Mar. 9, 1999; WO 91/14778, Donovan et al., published Oct. 3, 1991; WO 99/31248, English et al., published Jtine 24, 1999; WO 01/12731, Bice et al., published Feb. 22, 2001; WO 99/24581, Cardineau et al., published May 20, 1999; WO 97/40162, Narva et al., published Oct. 30, 1997; and U.S. Pub. Nos. 2002/0151709, Abad et al., published Oct. 17, 2002; 2003/0177528, Abad et al., published Sep. 18, 2003; and 2004/0091500, Ipsen et al., published May 13, 2004.

(E) An insect-specific hormone or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(F) An insect-specific peptide which, upon expression, disrupts the physiology of the affected pest. For example, see the disclosures of Regan, J. Biol. Chem. 269: 9 (1994) (expression cloning yields DNA coding for insect diuretic hormone receptor); Pratt et al., Biochem. Biophys. Res. Comm. 163: 1243 (1989) (an allostatin is identified in *Diploptera puntata*); Chattopadhyay et al. (2004) Critical Reviews in Microbiology 30 (1): 33-54 2004; Zjawiony (2004) J Nat Prod 67 (2): 300-310; Carlini & Grossi-de-Sa (2002) Toxicon, 40 (11):1515-1539; Ussuf et al. (2001) Curr Sci. 80 (7): 847-853; and Vasconcelos & Oliveira (2004) Toxicon 44 (4): 385-403. See also U.S. Pat. No. 5,266,317, Tomalski et al., issued Nov. 30, 1993, disclosing genes encoding insect-specific toxins.

(G) An enzyme responsible for an hyperaccumulation of a monterpene, a sesquiterpene, a steroid, hydroxamic acid, a phenylpropanoid derivative or another non-protein molecule with insecticidal activity.

(H) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197, Scott et al., published Feb. 4, 1993 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23: 691 (1993), who teach the nucleotide sequence of a cDNA encoding tobacco hookworm chitinase, and Kawalleck et al., Plant Molec. Biol. 21: 673 (1993), who provide the nucleotide sequence of the parsley ubi4-2 polyubiquitin gene, U.S. Pat. Nos. 7,145,060, Muller et al., issued Dec. 5, 2006; 7,087,810, Muller et al., issued Aug. 8, 2006; and 6,563,020, Simmons et al., issued May 13, 2003.

(I) A molecule that stimulates signal transduction. For example, see the disclosure by Botella et al., Plant Molec. Biol. 24: 757 (1994), of nucleotide sequences for mung bean calmodulin cDNA clones, and Griess et al., Plant Physiol. 104: 1467 (1994), who provide the nucleotide sequence of a maize calmodulin cDNA clone.

(J) A hydrophobic moment peptide. See WO 95/16776, Putman et al., published Jun. 22, 1995, and U.S. Pat. No. 5,580,852, Putnam et al., issued Dec. 3, 1996 (disclosure of peptide derivatives of Tachyplesin which inhibit fungal plant pathogens) and WO 95/18855, Rao et al., published Jul. 13, 1995, and U.S. Pat. No. 5,607,914, Rao et al., issued Mar. 4, 1997 (teaches synthetic antimicrobial peptides that confer disease resistance).

(K) A membrane permease, a channel former or a channel blocker. For example, see the disclosure by Jaynes et al., Plant Sci. 89: 43 (1993), of heterologous expression of a cecropin-beta lytic peptide analog to render transgenic tobacco plants resistant to *Pseudomonas solanacearum*.

(L) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus.

(M) An insect-specific antibody or an immunotoxin derived therefrom. Thus, an antibody targeted to a critical metabolic function in the insect gut would inactivate an affected enzyme, killing the insect. Cf. Taylor et al, Abstract #497, Seventh Intl Symposium on Molecular Plant-Microbe Interactions (Edinburgh, Scotland, 1994) (enzymatic inactivation in transgenic tobacco via production of single-chain antibody fragments).

(N) A virus-specific antibody. See, for example, Tavladoraki et al., Nature 366: 469 (1993), who show that transgenic plants expressing recombinant antibody genes are protected from virus attack.

(O) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See Lamb et al., Bio/Technology 10: 1436 (1992). The cloning and characterization of a gene which encodes a bean endopolygalacturonase-inhibiting protein is described by Toubart et al., Plant J. 2: 367 (1992).

(P) A developmental-arrestive protein produced in nature by a plant. For example, Logemann et al., Bio/Technology 10: 305 (1992), have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, S., Current Biology, 5(2):128-131 (1995), Pieterse & Van Loon (2004) Curr. Opin. Plant Bio. 7(4):456-64 and Somssich (2003) Cell 11 3(7):81 5-6.

(R) Antifungal genes (Cornelissen and Melchers, Pl. Physiol. 101:709-712, (1993) and Parijs et al., Planta 183: 258-264, (1991) and Bushnell et al., Can. J. of Plant Path. 20(2):137-149 (1998). Also see U.S. Pat. No. 6,875,907, Simmons et al, issued Apr. 5, 2005.

(S) Detoxification genes, such as for fumonisin, beauvericin, moniliformin and zearalenone and their structurally related derivatives. For example, see U.S. Pat. No. 5,792,931, Duvick et al., issued Aug. 11, 1998.

(T) Cystatin and cysteine proteinase inhibitors. See U.S. Pat. No. 7,205,453, Altier et al., issued Apr. 17, 2007.

(U) Defensin genes. See WO 03/000863, Cahoon et al., published Jan. 3, 2003, and U.S. Pat. No. 6,911,577, Simmons et al., issued Jun. 28, 2005.

(V) Genes conferring resistance to nematodes. See WO 03/033651, Hu et al., published Apr. 24, 2003, and Urwin et. al., Planta 204:472-479 (1998), Williamson (1999) Curr Opin Plant Bio. 2(4):327-31.

2. Genes that confer resistance to a herbicide include one or more of those described as follows in (A)-(E):

(A) Acetohydroxy acid synthase, which has been found to make plants that express this enzyme resistant to multiple types of herbicides, has been introduced into a variety of plants (see, e.g., Hattori et al. (1995) Mol Gen Genet. 246: 419). Other genes that confer tolerance to herbicides include: a gene encoding a chimeric protein of rat cytochrome P4507A1 and yeast NADPH-cytochrome P450 oxidoreductase (Shiota et al. (1994) Plant Physiol Plant Physiol 106:17), genes for glutathione reductase and superoxide dismutase (Aono et al. (1995) Plant Cell Physiol 36:1687, and genes for various phosphotransferases (Datta et al. (1992) Plant Mol Biol 20:619).

(B) A herbicide that inhibits the growing point or meristem, such as an imidazalinone or a sulfonylurea. Exemplary genes in this category code for mutant ALS and AHAS enzyme as described, for example, by Lee et al., EMBO J. 7: 1241 (1988), and Mild et al., Theor. Appl. Genet. 80: 449 (1990), respectively. See also, U.S. Pat. Nos. 5,605,011, Bedbrook et al., issued Feb. 25, 1997; 5,013,659, Bedbrook et al., issued May 7, 1991; 5,141,870, Bedbrook et al., issued Aug. 25, 1992; 5,767,361, Dietrich, issued Jun. 16, 1998; 5,731,180, Dietrich, issued Mar. 24, 1998; 5,304,732, Anderson et al., issued Apr. 19, 1994; 4,761,373, Anderson et al, issued Aug. 2, 1988; 5,331,107, Anderson et al., issued Jul. 19, 1994; 5,928,937, Kakefuda et al., issued Jul. 27, 1999; and 5,378,824, Bedbrook et al., issued Jan. 3, 1995; and international publication WO 96/33270, Kakefuda et al., published Oct. 24, 1996, which are incorporated herein by reference for this purpose.

(C) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. No. 4,940,835, Shah et al., issued Jul. 10, 1990, which discloses the nucleotide sequence of a form of EPSPS which can confer glyphosate resistance. U.S. Pat. No. 5,627,061, Barry et al., issued May 6, 1997 also describes genes encoding EPSPS enzymes. See also U.S. Pat. Nos. 6,566,587, Lebrun et al., issued May 20, 2003; 6,338,961, DeRose et al., issued Jan. 15, 2002; 6,248,876, Barry et al., issued Jun. 19, 2001; 6,040,497, Spencer et al., issued Mar. 21, 2000; 5,804,425, Barry et al., issued Sep. 8, 1998; 5,633,435, Barry et al., issued May 27, 1997; 5,145,783, Kishore et al., issued Sep. 8, 1992; 4,971,908, Kishore et al., issued Nov. 20, 1990; 5,312,910, Kishore et al., issued May 17, 1994; 5,188,642, Shah et al., issued Feb. 23, 1993; 4,940,835, Shah et al., issued Jul. 10, 1990; 5,866,775, Eichholtz et al, issued Feb. 2, 1999; 6,225,114, Eichholtz et al, issued May 1, 2001; 6,130,366, Herrera-Estrella et al., issued Oct. 10, 2000; 5,310,667, Eichholtz et al., issued May 10, 1994; 4,535,060, Comai, issued Aug. 13, 1985; 4,769,061, Comai, issued Sep. 6, 1988; 5,633,448, Lebrun et al., issued May 27, 1997; 5,510,471, Lebrun et al., issued Apr. 23, 1996; RE 36,449, Lebrun et al., issued Dec. 14, 1999; RE 37,287, Lebrun et al., issued Jul. 17, 2001; and U.S. Pat. No. 5,491,288, Chaubet et al., issued Feb. 13, 1996; and EP 1173580, Hawkes et al., Jan. 23, 2002; WO 01/66704, Baerson et al., published Sep. 13, 2001; EP 1173581 and EP 1173582, Hawkes et al., published Jan. 23, 2002, which are incorporated herein by reference for this purpose. Glyphosate resistance is also imparted to plants that express a gene that encodes a glyphosate oxido-reductase enzyme as described more fully in U.S. Pat. Nos. 5,776,760, Barry et al., issued Jul. 7, 1998 and 5,463,175, Barry et al., issued Oct. 31, 1995, which are incorporated herein by reference for this purpose. In addition glyphosate resistance can be imparted to plants by the over expression of genes encoding glyphosate N-acetyltransferase. See, for example, U.S. Pat. No. 7,462,481, Castle et al., issued Dec. 9, 2008. A DNA molecule encoding a mutant aroA gene can be obtained under ATCC accession No. 39256, and the nucleotide sequence of the mutant gene is disclosed in U.S. Pat. No. 4,769,061, Comai, issued Sep. 6, 1988. European Publication No. EP 0333033, Kumada et al., published Sep. 20, 1989, and U.S. Pat. No. 4,975,374, Goodman et al., issued Dec. 4, 1990, disclose nucleotide sequences of glutamine synthetase genes which confer resistance to herbicides such as L-phosphinothricin. The nucleotide sequence of a phosphinothricin-acetyl-transferase gene is provided in EP 0242246 and EP 0242236, Leemans et al., published Oct. 21, 1987. De Greef et al., Bio/Technology 7: 61 (1989), describe the production of transgenic plants that express chimeric bar genes coding for phosphinothricin acetyl transferase activity. See also, U.S. Pat. Nos. 5,969,213, Adams et al., issued Oct. 19, 1999; 5,489,520, Adams et al., issued Feb. 6, 1996; 5,550,318, Adams et al., issued Aug. 27, 1996; 5,874,265, Adams et al., issued Feb. 23, 1999; 5,919, 675, Adams et al., issued Jul. 6, 1999; 5,561,236, Leemans et al., issued Oct. 1, 1996; 5,648,477, Leemans et al., issued Jul. 15, 1997; 5,646,024, Leemans et al., issued Jul. 8, 1997; 6,177,616, Bartsch et al., issued Jan. 23, 2001; and U.S. Pat. No. 5,879,903, Strauch et al., issued Mar. 9, 1999, which are incorporated herein by reference for this purpose. Exemplary genes conferring resistance to phenoxy proprionic acids and cycloshexones, such as sethoxydim and haloxyfop, are the Acc1-S1, Acc1-S2 and Acc1-S3 genes described by Marshall et al., Theor. Appl. Genet. 83: 435 (1992).

(D) An herbicide that inhibits photosynthesis, such as a triazine (psbA and gs+genes) and a benzonitrile (nitrilase gene). Przibilla et al., Plant Cell 3: 169 (1991), describe the transformation of *Chlamydomonas* with plasmids encoding mutant psbA genes. Nucleotide sequences for nitrilase genes are disclosed in U.S. Pat. No. 4,810,648, Stalker, issued Mar. 7, 1989, and DNA molecules containing these genes are available under ATCC Accession Nos. 53435, 67441 and 67442. Cloning and expression of DNA coding for a glutathione S-transferase is described by Hayes et al., Biochem. J. 285: 173 (1992).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306, Ward et al., issued Sep. 11, 2001; 6,282,837, Ward et al., issued Sep. 4, 2001; and 5,767,373; Ward et al., issued Jun. 16, 1998; and WO 01/12825, Johnson et al., published Feb. 22, 2001.

3. Genes that confer or improve grain quality include one or more of those described as follows in (A)-(E):

(A) Altered fatty acids, for example, by (1) Down-regulation of stearoyl-ACP desaturase to increase stearic acid content of the plant. See Knultzon et al., Proc. Natl. Acad. Sci. USA 89: 2624 (1992) and WO 99/64579, Shen, published Dec. 16, 1999 (Genes for Desaturases to Alter Lipid Profiles in Corn), (2) Elevating oleic acid via FAD-2 gene modification and/or decreasing linolenic acid via FAD-3 gene modification (see U.S. Pat. Nos. 6,063,947, DeBonte et al., issued May 16, 2000; 6,323,392, Charne, issued Nov. 27, 2001; 6,372,965, Lightner et al., issued Apr. 16, 2002, and WO 93/11245, Browse et al., published Jun. 10, 1993), (3) Altering conjugated linolenic or linoleic acid content, such as in WO 01/12800, Cahoon et al., published Feb. 22, 2001, (4) Altering LEC1, AGP, Dek1, Superal1, mi1ps, various lpa genes such as lpa1, lpa3, hpt or hggt. For example, see WO 02/42424, Lappegard, published May 30, 2002; WO 98/22604, Singletary et al., published May 28, 1998; WO 03/011015, Tarczynski et al., published Feb. 13, 2003; U.S. Pat. Nos. 6,423,886; Singletary et al., issued Jul. 23, 2002; 6,197,561, Martino-Catt et al., issued Mar. 6, 2001; 6,825,397, Lowe et al., issued Nov. 30, 2004; U.S. Pub. Nos. 2003/0079247, Shi et al., published Apr. 24, 2003; 2003/0204870, Allen et al., published Oct. 30, 2003; WO 02/057439, Cahoon et al., published Jul. 25, 2002; WO 03/011015, Tarczynski et al., published Feb. 13, 2003; and Rivera-Madrid, R. et al., Proc. Natl. Acad. Sci. 92:5620-5624 (1995).

(B) Altered phosphorus content, for example, by the (1) Introduction of a phytase-encoding gene would enhance breakdown of phytate, adding more free phosphate to the transformed plant. For example, see Van Hartingsveldt et al., Gene 127: 87 (1993), for a disclosure of the nucleotide sequence of an *Aspergillus niger* phytase gene. (2) Up-regulation of a gene that reduces phytate content. In maize, this, for example, could be accomplished, by cloning and then re-introducing DNA associated with one or more of the alleles, such as the LPA alleles, identified in maize mutants characterized by low levels of phytic acid, such as in Raboy et al., Maydica 35: 383 (1990) and/or by altering inositol kinase activity as in WO 02/059324, Shi et al., published Aug. 1, 2002; U.S. Pub. No. 2003/0009011, Shi et al., published Jan. 9, 2003; WO 03/027243, Shi et al., published Apr. 3, 2003; U.S. Pub. No. 2003/0079247, Shi et al., published Apr. 24, 2003; WO 99/05298, Martino-Catt et al., published Feb. 4, 199; U.S. Pat. Nos. 6,197,561, Martino-Catt et al., issued Mar. 6, 2001; 6,291,224, Martino-Catt et al., issued Sep. 18, 2001; 6,391,348, Stilborn et al., issued May 21, 2002; WO 2002/059324, Shi et al., published Aug. 1, 2002; WO 98/45448, Hitz et al., published Oct. 15, 1998; WO 99/55882, Cahoon et al., published Nov. 4, 1999; and WO 01/04147, Cahoon, published Jan. 18, 2001.

(C) Altered carbohydrates effected, for example, by altering a gene for an enzyme that affects the branching pattern of starch or a gene altering thioredoxin (See U.S. Pat. No. 6,531,648, Lanahan et al., issued Mar. 11, 2003). See Shiroza et al., J. Bacteriol. 170: 810 (1988) (nucleotide sequence of *Streptococcus mutans* fructosyltransferase gene), Steinmetz et al., Mol. Gen. Genet. 200: 220 (1985) (nucleotide sequence of *Bacillus subtilis* levansucrase gene), Pen et al., Bio/Technology 10: 292 (1992) (production of transgenic plants that express *Bacillus lichenifomis* alpha-amylase), Elliot et al., Plant Molec. Biol. 21: 515 (1993) (nucleotide sequences of tomato invertase genes), Sogaard et al., J. Biol. Chem. 268: 22480 (1993) (site-directed mutagenesis of barley alpha-amylase gene), and Fisher et al., Plant Physiol. 102: 1045 (1993) (maize endosperm starch branching enzyme II), WO 99/10498, Helentjaris et al., published Mar. 4, 1999 (improved digestibility and/or starch extraction through modification of UDP-D-xylose 4-epimerase, Fragile 1 and 2, Ref1, HCHL, C4H), U.S. Pat. No. 6,232,529, Singletary et al., issued May 15, 2001, (method of producing high oil seed by modification of starch levels (AGP)). The fatty acid modification genes mentioned above may also be used to affect starch content and/or composition through the interrelationship of the starch and oil pathways.

(D) Altered antioxidant content or composition, such as alteration of tocopherol or tocotrienols. For example, see U.S. Pat. No. 6,787,683, Penna et al., issued Sep. 7, 2004; U.S. Pub. No. 2004/0034886, Cahoon et al., published Feb. 19, 2004; and WO 00/68393, Della Penna et al., published Nov. 16, 2000, involving the manipulation of antioxidant levels through alteration of a phytl prenyl transferase (ppt), WO 03/082899, Cahoon et al., published Oct. 9, 2003, through alteration of a homogentisate geranyl geranyl transferase (hggt).

(E) Altered essential seed amino acids. For example, see U.S. Pat. Nos. 6,127,600, Beach et al., issued Oct. 3, 2000 (method of increasing accumulation of essential amino acids in seeds); 6,080,913, Tarczynski et al., issued Jun. 27, 2000 (binary methods of increasing accumulation of essential amino acids in seeds); 5,990,389, Rao et al., issued Nov. 23, 1999 (high lysine); WO 99/40209, Jung et al., published Aug. 12, 1999 (alteration of amino acid compositions in seeds); WO 99/29882, Rao et al., published Jun. 17, 1999 (methods for altering amino acid content of proteins); U.S. Pat. No. 5,850,016, Jung et al., issued Dec. 15, 1998 (alteration of amino acid compositions in seeds); WO 98/20133, Rao et al., published May 14, 1998 (proteins with enhanced levels of essential amino acids); U.S. Pat. Nos. 5,885,802, Rao, issued Mar. 23, 1999 (high methionine); 5,885,801, Rao, issued Mar. 23, 1999 (high threonine); 6,664,445, Falco et al., issued Dec. 16, 2003 (plant amino acid biosynthetic enzymes); 6,459,019, Falco, issued Oct. 1, 2002 (increased lysine and threonine); 6,441,274, Cahoon et al., issued Aug. 27, 2002 (plant tryptophan synthase beta subunit); 6,346,403, Rafalski et al., issued Feb. 12, 2002 (methionine metabolic enzymes); 5,939,599, Chui et al., issued Aug. 17, 1999 (high sulfur); 5,912,414, Falco et al., issued Jun. 15, 1999 (increased methionine); WO 98/56935, Falco et al., Dec. 17, 1998 (plant amino acid biosynthetic enzymes); WO 98/45458, Gutteridge, published Oct. 15, 1998 (engineered seed protein having higher percentage of essential amino acids); WO 98/42831, Falco et al., published Oct. 1, 1998 (increased lysine); U.S. Pat. No. 5,633,436, Wandelt, issued May 27, 1997 (increasing sulfur amino acid content); U.S. Pat. No. 5,559,223, Falco et al., issued Sep. 24, 1996 (synthetic storage proteins with defined structure containing programmable levels of essential amino acids for improvement of the nutritional value of plants); WO 96/01905, Falco, published Jan. 25, 1996 (increased threonine); WO 95/15392, Falco et al., Jun. 8, 1995 (increased lysine); U.S. Pub. Nos. 2003/0163838, Dhugga et al., published Aug. 28, 2003; 2003/0150014, Dhugga et al., published Aug. 7, 2003; 2004/0068767, Dhugga et al., published Apr. 8, 2004; U.S. Pat. No. 6,803,498, Dhugga et al., issued Oct. 12, 2004; WO 01/79516, Dhugga et al., published Oct. 25, 2001; and WO 00/09706, Dhugga et al., published Feb. 24, 2000 (Ces A: cellulose synthase); U.S. Pat. Nos. 6,194,638, Dhugga et al., issued Feb. 27, 2001 (hemicellulose); 6,399,859, Nichols et al., issued Jun. 4, 2002; and U.S. Pub. No. 2004/0025203, Singletary et al., published Feb. 5, 2004 (UDPGdH).

4. Genes that control male-sterility.

There are several methods of conferring genetic male sterility available, such as multiple mutant genes at separate locations within the genome that confer male sterility, as disclosed in U.S. Pat. Nos. 4,654,465, Brar et al., issued Mar. 31, 1987; and 4,727,219, Brar et al., issued Feb. 23, 1988 and chromosomal translocations as described by Patterson in U.S. Pat. Nos. 3,861,079, Patterson, issued Jan. 21, 1975, and 3,710,511, Patterson, issued Jan. 16, 1973. In addition to these methods, U.S. Pat. No. 5,432,068, Albertsen et al., issued Jul. 11, 1995, describes a system of nuclear male sterility which includes identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

Such genes and methods include one or more of those described as follows in (A)-(C).

(A) Introduction of a deacetylase gene under the control of a tapetum-specific promoter and with the application of the chemical N-Ac-PPT (WO 01/29237, Quandt et al., published Apr. 26, 2001).

(B) Introduction of various stamen-specific promoters (WO 92/13956, Michiels et al., published Aug. 20, 1992; WO 92/13957, DeBeuckeleer et al., published Aug. 20, 1992).

(C) Introduction of the barnase and the barstar gene (Paul et al. Plant Mol. Biol. 19:611-622, 1992).

For additional examples of nuclear male and female sterility systems and genes, see also, U.S. Pat. Nos. 5,859,341, Albertsen et al., issued Jan. 12, 1999; 6,297,426, Albertsen et al., issued Oct. 2, 2001; 5,478,369, Albertsen et al., issed Dec. 26, 1995; 5,824,524, Albertsen et al., issued Oct. 20, 1998; 5,850,014, Albertsen et al., issued Dec. 15, 1998; 6,265,640, Albertsen et al., issued Jul. 24, 2001; all of which are hereby incorporated by reference.

5. Genes that create a site for site specific DNA integration.

This includes the introduction of FRT sites that may be used in the FLP/PRT system and/or Lox sites that may be used in the Cre/Loxp system. For example, see Lyznik, et al., Site-Specific Recombination for Genetic Engineering in Plants, Plant Cell Rep (2003) 21:925-932 and WO 99/25821, Baszczynski et al., published May 27, 1999, which are hereby incorporated by reference. Other systems that may be used include the Gin recombinase of phage Mu (Maeser et al., 1991; Vicki Chandler, The Maize Handbook ch. 118 (Springer-Verlag 1994), the Pin recombinase of E. coli (Enomoto et al., 1983), and the R/RS system of the pSRi plasmid (Araki et al., 1992).

6. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress.

For example, see: WO 00/73475, LaPorte et al., published Dec. 7, 2000, where water use efficiency is altered through alteration of malate; U.S. Pat. Nos. 5,892,009, Thomashow et al, issued Apr. 6, 1999; 5,965,705, Thomashow et al., issued Oct. 12, 1999; 5,929,305, Thomashow et al., issued Jul. 27, 1999; 5,891,859, Thomashow et al., issued Apr. 6, 1999; 6,417,428, Thomashow et al., issued Jul. 9, 2002; 6,664,446, Heard et al., issued Dec. 16, 2003; 6,706,866, Thomashow et al., issued Mar. 16, 2004; 6,717,034, Jiang, issued Apr. 6, 2004; 6,801,104, Zhu et al., issued Oct. 5, 2004; WO 2000/060089, Fromm et al., published Oct. 12, 2000; WO 2001/026459, Ratcliffe et al., published Apr. 19, 2001; WO 2001/035725, Jiang et al., published May 25, 2001; WO 2001/035727, Rueber et al., published May 25, 2001; WO 2001/036444, Riechmann et al., published May 25, 2001; WO 2001/036597, Creelman et al., published May 25, 2001; WO 2001/036598, Pineda et al., published May 25, 2001; WO 2002/015675, Pilgrim et al., Feb. 28, 2002; WO 2002/077185, Reuber, published Oct. 3, 2002; WO 2002/079403, Cai-Zhong, published Oct. 10, 2002; WO 2003/013227, Ratcliffe et al., published Feb. 20, 2003; WO 2003/013228, Heard et al., published Feb. 20, 2003; WO 2003/014327, Reuber et al., published Feb. 20, 2003; WO 2004/031349, Jiang et al., published Apr. 15, 2004; WO 2004/076638, Sherman et al., published Sep. 10, 2004; WO 98/09521, Thomashow et al., published Mar. 12, 1998; and WO 99/38977, Stockinger et al., published Aug. 5, 1999, describing genes, including CBF genes and transcription factors effective in mitigating the negative effects of freezing, high salinity, and drought on plants, as well as conferring other positive effects on plant phenotype; U.S. Pub. No. 2004/0148654, Helentjaris, published Jul. 29, 2004 and WO 01/36596, Helentjaris, published May 25, 2001, where abscisic acid is altered in plants resulting in improved plant phenotype such as increased yield and/or increased tolerance to abiotic stress; WO 2000/063401, Habben et al., published Oct. 26, 2000; WO 04/090143, Habben et al., published Oct. 21, 2004; U.S. Pub. No. 2004/0237147, Habben et al., published Nov. 25, 2004; and U.S. Pat No. 6,992,237, Habben et al., issued Jan. 31, 2006, where cytokinin expression is modified resulting in plants with increased stress tolerance, such as drought tolerance, and/or increased yield. Also see WO 0202776, Tiam et al., published Jan. 10, 2002; WO 2003/052063, Campbell et al., published Jun. 26, 2003; JP 2002281975, Hitoshi et al., published Oct. 2, 2002; U.S. Pat. No. 6,084,153, Good et al., issued Jul. 4, 2000; WO 01/64898, Odom et al., published Sep. 7, 2001; U.S. Pat. Nos. 6,177,275, Coruzzi et al., issued Jan. 23, 2001 and 6,107,547, Coruzzi et al., issued Aug. 22, 2000 (enhancement of nitrogen utilization and altered nitrogen responsiveness). For ethylene alteration, see U.S. Pub. Nos. 2004/0128719, Klee et al., published Jul. 1, 2004; 2003/0166197, Ecker et al., published Sep. 4, 2003; and WO 2000/32761, Ecker et al., published Jun. 8, 2000. For plant transcription factors or transcriptional regulators of abiotic stress, see e.g. U.S. Pub. Nos. 2004/0098764, Heard et al., published May 20, 2004; or 2004/0078852, Thomashow et al., published, Apr. 22, 2004.

Other genes and transcription factors that affect plant growth and agronomic traits such as yield, flowering, plant growth and/or plant structure, can be introduced or introgressed into plants, see e.g. WO 97/49811, Coupland et al., published Dec. 31, 1997; (LHY); WO 98/56918, Coupland, published Dec. 17, 1998 (ESD4); WO 97/10339, Bradley et al., published Mar. 20, 1997; and U.S. Pat. Nos. 6,573,430, Bradley et al., issued Jun. 3, 2003 (TFL); 6,713,663, Weigel et al., issued Mar. 30, 20044 ($F_7$); WO 96/14414, Coupland et al., published May 17, 1996 (CON); WO 96/38560, Dean et al., published Dec. 5, 1996; WO 01/21822, Dean et al., published Mar. 29, 2001 (VRN1); WO 00/44918, Dean et al., published Aug. 3, 2000 (VRN2); WO 99/49064, Coupland et al., published Sep. 30, 1999 (GI); WO 00/46358, Johanson et al., published Aug. 10, 2000 (FR1); WO 97/29123, Harberd et al., published Aug. 14, 1997; U.S. Pat. Nos. 6,794,560, Harberd et al., issued Sep. 21, 2004; 6,307,126, Harberd et al., issued Oct. 23, 2001 (GAI); WO 99/09174, Harberd et al., published Feb. 25, 1999 (D8 and Rht); and WO 2004/076638, Sherman et al., published Sep. 10, 2004; and WO 2004/031349, Jiang et al., published Apr. 15, 2004 (transcription factors).

7. Genes that confer agronomic enhancements, nutritional enhancements, or industrial enhancements include one or more of those described as follows in (A) and (B).

(A) Improved tolerance to water stress from drought or high salt water condition. The HVA1 protein belongs to the group 3 LEA proteins that include other members such as wheat pMA2005 (Curry et al., 1991; Curry and Walker-Simmons, 1993), cotton D-7 (Baker et al., 1988), carrot Dc3 (Seffens et al., 1990), and rape pLEA76 (Harada et al., 1989). These proteins are characterized by 11-mer tandem repeats of amino acid domains which may form a probable amphophilic alpha-helical structure that presents a hydrophilic surface with a hydrophobic stripe (Baker et al., 1988; Dure et al., 1988; Dure, 1993). The barley HVA1 gene and the wheat pMA2005 gene (Curry et al., 1991; Curry and Walker-Simmons, 1993) are highly similar at both the nucleotide level and predicted amino acid level. These two monocot genes are closely related to the cotton D-7 gene (Baker et al., 1988) and carrot Dc3 gene (Seffens et al., 1990) with which they share a similar structural gene organization (Straub et al., 1994). There is, therefore, a correlation between LEA gene expression or LEA protein accumulation with stress tolerance in a number of plants. For example, in severely dehydrated wheat seedlings, the accumulation of high levels of group 3 LEA proteins was correlated with tissue dehydration tolerance (Ried and Walker-Simmons, 1993). Studies on several Indica varieties of rice showed that the levels of group 2 LEA proteins (also known as dehydrins) and group 3 LEA proteins in roots were significantly higher in salt-tolerant varieties compared with sensitive varieties (Moons et al., 1995). The barley HVA1 gene was transformed into wheat. Transformed wheat plants showed increased tolerance to water stress, (Sivamani, E. et al. Plant Science 2000, V.155 pl-9 and U.S. Pat. No. 5,981,842, Wu et al., issued Nov. 9, 1999.)

(B) Another example of improved water stress tolerance is through increased mannitol levels via the bacterial mannitol-1-phosphate dehydrogenase gene. To produce a plant with a genetic basis for coping with water deficit, Tarczynski et al. (Proc. Natl. Acad. Sci. USA, 89, 2600 (1992); WO 92/19731, Tarczynski et al., published Nov. 12, 1992; Science, 259, 508 (1993)) introduced the bacterial mannitol-1-phosphate dehydrogenase gene, mtlD, into tobacco cells via *Agrobacterium*-mediated transformation. Root and leaf tissues from transgenic plants regenerated from these transformed tobacco cells contained up to 100 mM mannitol. Control plants contained no detectable mannitol. To determine whether the transgenic tobacco plants exhibited increased tolerance to water deficit, Tarczynski et al. compared the growth of transgenic plants to that of untransformed control plants in the presence of 250 mM NaCl. After 30 days of exposure to 250 mM NaCl, transgenic plants had decreased weight loss and increased height relative to their untransformed counterparts. The authors concluded that the presence of mannitol in these transformed tobacco plants contributed to water deficit tolerance at the cellular level. See also U.S. Pat. No. 5,780,709, Adams et al., issued Jul. 14, 1998, and WO 92/19731, Tarczynski et al., published Nov. 12, 1992, which are incorporated herein by reference for this purpose.

Numerous methods for plant transformation have been developed, including biological and physical, plant transformation protocols. See, for example, Mild et al., "Procedures for Introducing Foreign DNA into Plants" in Methods in Plant Molecular Biology and Biotechnology, Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, Inc., Boca Raton, 1993) pages 89-119.

Further embodiments of the present technology are the treatment of E0028 with a mutagen and the plant produced by mutagenesis of E0028. Information about mutagens and mutagenizing seeds or pollen are presented in the IAEA's Manual on Mutation Breeding (IAEA, 1977) other information about mutation breeding in wheat can be found in C. F. Konzak, "Mutations and Mutation Breeding" chapter 7B, of Wheat and Wheat Improvement, 2nd edition, Ed. Heyne, 1987.

A further embodiment is a backcross conversion of MSU Line E0028. A backcross conversion occurs when DNA sequences are introduced through traditional (non-transformation) breeding techniques, such as backcrossing. DNA sequences, whether naturally occurring or transgenes, may be introduced using these traditional breeding techniques. Desired traits transferred through this process include, but are not limited to nutritional enhancements, industrial enhancements, disease resistance, insect resistance, herbicide resistance, agronomic enhancements, grain quality enhancement, waxy starch, breeding enhancements, seed production enhancements, and male sterility. Descriptions of some of the cytoplasmic male sterility genes, nuclear male sterility genes, chemical hybridizing agents, male fertility restoration genes, and methods of using the aforementioned are discussed in "Hybrid Wheat by K. A. Lucken (pp. 444-452 In Wheat and Wheat Improvement, ed. Heyne, 1987). Examples of genes for other traits include: Leaf rust resistance genes (Lr series such as Lr1, Lr10, Lr21, Lr22, Lr22a, Lr32, Lr37, Lr41, Lr42, and Lr43), *Fusarium* head blight-resistance genes (QFhs.ndsu-3B and QFhs.ndsu-2A), Powdery Mildew resistance genes (Pm21), common bunt resistance genes (Bt-10), and wheat streak mosaic virus resistance gene (Wsm1), Russian wheat aphid resistance genes (Dn series such as Dn1, Dn2, Dn4, Dn5), Black stem rust resistance genes (Sr38), Yellow rust resistance genes (Yr series such as Yr1, YrSD, Yrsu, Yr17, Yr15, YrH52), Aluminum tolerance genes (Alt(BH)), dwarf genes (Rht), vernalization genes (Vrn), Hessian fly resistance genes (H9, H10, H21, H29), grain color genes (R/r), glyphosate resistance genes (EPSPS), glufosinate genes (bar, pat) and water stress tolerance genes (Hva1, mtlD). The trait of interest is transferred from the donor parent to the recurrent parent, in this case, the wheat plant disclosed herein. Single gene traits may result from either the transfer of a dominant allele or a recessive allele. Selection of progeny containing the trait of interest is done by direct selection for a trait associated with a dominant allele. Selection of progeny for a trait that is transferred via a recessive allele requires growing and selfing the first backcross to determine which plants carry the recessive alleles. Recessive traits may require additional progeny testing in successive backcross generations to determine the presence of the gene of interest.

Another embodiment of this technology is a method of developing a backcross conversion E0028 wheat plant that involves the repeated backcrossing to MSU Line E0028. The number of backcrosses made may be 2, 3, 4, 5, 6 or greater, and the specific number of backcrosses used will depend upon the genetics of the donor parent and whether molecular markers are utilized in the backcrossing program. See, for example, R. E. Allan, "Wheat" in Principles of Cultivar Development, Fehr, W. R. Ed. (Macmillan Publishing Company, New York, 1987) pages 722-723, incorporated herein by reference. Using backcrossing methods, one of ordinary skill in the art can develop individual plants and populations of plants that retain at least 70%, 75%, 79%, 80%, 81%, 82%, 83%, 84%, 85%, 86%, 87%, 88%, 89%, 90%, 91%, 92%, 93%, 94%, 95%, 96%, 97%, 98%, or 99% of the genetic profile of MSU Line E0028. The percentage of the genetics retained in the backcross conversion may be measured by either pedigree analysis or through the use of genetic techniques such as molecular markers or electrophoresis. In pedigree analysis, on average 50% of the starting germplasm would be passed to the progeny line after one cross to another line, 75% after backcrossing once, 87.5% after backcrossing twice, and so on. Molecular markers could also be used to confirm and/or determine the recurrent parent used. The backcross conversion developed from this method may be similar to E0028. Such similarity may be measured by a side by side phenotypic comparison, with differences and similarities determined at a 5% significance level. Any such comparison should be made in environmental conditions that account for the trait being transferred. For example, herbicide should not be applied in the phenotypic comparison of herbicide resistant backcross conversion of E0028 to E0028.

Another embodiment of the technology is an essentially derived variety of E0028. As determined by the UPOV Convention, essentially derived varieties may be obtained for example by the selection of a natural or induced mutant, or of a somaclonal variant, the selection of a variant individual from plants of the initial variety, backcrossing, or transformation by genetic engineering. An essentially derived variety of E0028 is further defined as one whose production requires the repeated use of variety E0028 or is predominately derived from variety E0028. International Convention for the Protection of New Varieties of Plants, as amended on Mar. 19, 1991, Chapter V, Article 14, Section 5(c).

This technology is also directed to methods for using MSU Line E0028 in plant breeding. One such embodiment is the method of crossing MSU Line E0028 with another variety of wheat to form a first generation population of F1 plants. The population of first generation F1 plants produced by this method is also an embodiment of the present technology. This first generation population of F1 plants will comprise an essentially complete set of the alleles of MSU Line E0028. One of ordinary skill in the art can utilize either breeder books or molecular, methods to identify a particular F1 plant produced using MSU Line E0028, and any such individual plant is also encompassed by this technology. These embodiments also cover use of transgenic or backcross conversions of MSU Line E0028 to produce first generation $F_1$ plants.

A method of developing a E0028-progeny wheat plant comprising crossing E0028 with a second wheat plant and performing a breeding method is also an embodiment of the present technology. A specific method for producing a line derived from MSU Line E0028 is as follows. One of ordinary skill in the art would cross MSU Line E0028 with another variety of wheat, such as an elite variety. The F1 seed derived from this cross would be grown to form a homogeneous population. The F1 seed would contain one set of the alleles from variety E0028 and one set of the alleles from the other wheat variety. The F1 genome would be made-up of 50% variety E0028 and 50% of the other elite variety. The F1 seed would be grown and allowed to self, thereby forming F2 seed. On average the F2 seed would have derived 50% of its alleles from variety E0028 and 50% from the other wheat variety, but various individual plants from the population would have a much greater percentage or much lower percentage of their alleles derived from E0028. See Wang J. and R. Bernardo, 2000, Crop Sci. 40:659-665 and Bernardo, R. and A. L. Kahler, 2001, Theor. Appl. Genet. 102:986-992. The $F_2$ seed would be grown and selection of plants would be made based on visual observation and/or measurement of traits. The E0028-derived progeny that exhibit one or more of the desired E0028-derived traits would be selected and each plant would be harvested separately. This F3 seed from each plant would be grown in individual rows and allowed to self. Then selected rows or plants from the rows would be harvested and threshed individually. The selections would again be based on visual observation and/or measurements for desirable traits of the plants, such as one or more of the desirable E0028-derived traits. The process of growing and selection would be repeated any number of times until a homozygous E0028-derived wheat plant is obtained. The homozygous E0028-derived wheat plant would contain desirable traits derived from MSU Line E0028, some of which may not have been expressed by the other original wheat variety to which MSU Line E0028 was crossed and some of which may have been expressed by both wheat varieties but now would be at a level equal to or greater than the level expressed in MSU Line E0028. The homozygous E0028-derived wheat plants would have, on average, 50% of their genes derived from MSU Line E0028, but various individual plants from the population would have a much greater percentage of their alleles derived from E0028. The breeding process, of crossing, selfing, and selection may be repeated to produce another population of E0028-derived wheat plants with, on average, 25% of their genes derived from MSU Line E0028, but various individual plants from the population would have a much greater percentage of their alleles derived from E0028. Another embodiment of the present technology is a homozygous E0028-derived wheat plant that has received E0028-derived traits.

The previous example can be modified in numerous ways, for instance selection may or may not occur at every selfing generation, selection may occur before or after the actual self-pollination process occurs, or individual selections may be made by harvesting individual spikes, plants, rows or plots at any point during the breeding process described. In addition, double haploid breeding methods may be used at any step in the process. The population of plants produced at each and any generation of selfing is also an embodiment of the present technology, and each such population would consist of plants containing approximately 50% of its genes from MSU Line E0028, 25% of its genes from MSU Line E0028 in the second cycle of crossing, selfing, and selection, 12.5% of its genes from MSU Line E0028 in the third cycle of crossing, selfing, and selection, and so on.

Another embodiment of this technology is the method of obtaining a homozygous E0028-derived wheat plant by crossing MSU Line E0028 with another variety of wheat and applying double haploid methods to the F1 seed or F1 plant or to any generation of E0028-derived wheat obtained by the selfing of this cross.

Still further, this technology also is directed to methods for producing E0028-derived wheat plants by crossing MSU Line E0028 with a wheat plant and growing the progeny seed, and repeating the crossing or selfing along with the growing steps with the E0028-derived wheat plant from 1 to 2 times, 1 to 3 times, 1 to 4 times, or 1 to 5 times. Thus, any and all methods using MSU Line E0028 in breeding are part of this technology, including selfing, pedigree breeding, backcrossing, hybrid production and crosses to populations. Unique starch profiles, molecular marker profiles and/or breeding records can be used by those of ordinary skill in the art to identify the progeny lines or populations derived from these breeding methods.

In addition, this technology also encompasses progeny with the same or greater yield or test weight of E0028, the same or shorter plant height, and the same or greater resistance to leaf rust, powdery mildew, leaf blight, and spindle streak mosaic virus of E0028. The expression of these traits may be measured by a side by side phenotypic comparison, with differences and similarities determined at a 5% significance level. Any such comparison should be made in the same environmental conditions.

In conjunction with the present technology, a deposit is made of at least 2500 seeds of MSU Line E0028 with the American Type Culture Collection (ATCC), Manassas, Va. 20110 USA, ATCC Patent Deposit Designation PTA-10223. The seeds were deposited with the ATCC on Jul. 16, 2009. The deposit was tested on Jul. 27, 2009 and on that date, the seeds were viable. Access to this deposit will be available during the pendency of the application to the Commissioner of Patents and Trademarks and persons determined by the Commissioner to be entitled thereto upon request.

Upon issue of claims, the Applicant will make available to the public, pursuant to 37 CFR 1.808, a deposit of at least 2500 seeds of variety E0028 with the American type Culture Collection (ATCC), 10801 University Boulevard, Manassas, Va. 20110-2209. This deposit of the MSU Line E0028 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has or will satisfy all the requirements of 37 C.F.R. §§1.801-1.809, including providing an indication of the viability of the sample. Applicant has no authority to waive any restrictions imposed by law on the transfer of biological material or its transportation in commerce. Applicant does not waive any infringement of their rights granted under this patent or under the Plant Variety Protection Act (7 USC 2321 et seq.).

MSU Line E0028 is registered and described in the Journal of Plant Registrations in a publication entitled "Registration of 'Ambassador' Wheat," which is incorporated herein by reference.

The embodiments described herein are exemplary and not intended to be limiting in describing the full scope of compositions and methods of the present technology. Equivalent changes, modifications and variations of embodiments, materials, compositions and methods can be made within the scope of the present technology, with substantially similar results.

What is claimed is:

1. A seed of soft winter white wheat variety designated E0028, representative seed of variety E0028 deposited under American Type Culture Collection (ATCC) Patent Deposit Designation PTA-10223.

2. A wheat plant or a portion of a wheat plant produced by growing the seed of claim 1.

3. A tissue culture of regenerable cells produced from the plant of claim 2.

4. A protoplast produced from the tissue culture of claim 3.

5. The tissue culture of claim 3, wherein cells of the tissue culture are produced from a tissue selected from the group consisting of kernel, head, stem, leaves, root, root tip, pollen, ovule, embryo, and flower.

6. A wheat plant regenerated from the tissue culture of claim 3, the wheat plant having all the morphological and physiological characteristics of MSU Line E0028, representative seed of said wheat variety deposited under ATCC Patent Deposit Designation PTA-10223.

7. A method for producing an F1 wheat seed, comprising crossing the wheat plant of claim 2 with a different wheat plant and harvesting the resulting F1 wheat seed.

8. A method of producing a male sterile wheat plant comprising transforming the wheat plant of claim 2 with a nucleic acid molecule that confers male sterility.

9. A male sterile wheat plant produced by the method of claim 8.

10. A method of producing an herbicide-resistant wheat plant comprising transforming the wheat plant of claim 2 with a transgene that confers herbicide resistance.

11. An herbicide resistant wheat plant produced by the method of claim 10.

12. The wheat plant of claim 11, wherein the transgene confers resistance to an herbicide selected from the group consisting of imidazalinone, sulfonylurea, glyphosate, glufosinate, L-phosphinothricin, triazine and benzonitrile.

13. A method of producing an insect-resistant wheat plant comprising transforming the wheat plant of claim 2 with a transgene that confers insect resistance.

14. An insect resistant wheat plant produced by the method of claim 13.

15. The wheat plant of claim 13, wherein the transgene encodes a *Bacillus thuringiensis* endotoxin.

16. A method of producing a disease-resistant wheat plant comprising transforming the wheat plant of claim 2 with a transgene that confers disease resistance.

17. A disease resistant wheat plant produced by the method of claim 16.

18. The wheat plant of claim 17, wherein the transgene confers resistance to *Fusarium graminearum* through the detoxification of deoxynivalenol.

19. A method of producing a wheat plant with decreased phytate content comprising transforming the wheat plant of claim 2 with a transgene encoding phytase.

20. A wheat plant with decreased phytate content produced by the method of claim 19.

21. A method of producing a wheat plant with modified fatty acid metabolism, modified protein metabolism or modified carbohydrate metabolism comprising transforming the wheat plant of claim 2 with a transgene encoding a polypeptide selected from the group consisting of modified glutenins, gliadins, fructosyltransferase, levansucrase, alpha-amylase, invertase and starch branching enzyme or encoding an antisense stearyl-ACP-desaturase.

22. A wheat plant with modified fatty acid metabolism, modified protein metabolism or modified carbohydrate metabolism produced by the method of claim 21.

23. The wheat plant of claim 22 wherein the transgene confers a trait selected from the group consisting of waxy starch and increased amylose starch.

24. A wheat plant or a portion of a wheat plant having all the physiological and morphological characteristics of the variety E0028, representative seed of such line having been deposited under ATCC Patent Deposit Designation PTA-10223.

25. A method of producing a wheat plant with increased tolerance to water stress comprising transforming the wheat plant of claim 2 with a transgene encoding mannitol-1-phosphate dehydrogenase or late embryogenesis abundant (LEA) proteins.

26. A wheat plant with increased tolerance to water stress produced by the method of claim 25.

27. A method of introducing a desired trait into MSU Line E0028 comprising:
   (a) crossing E0028 plants grown from E0028 seed, representative seed of which has been deposited under ATCC Patent Deposit Designation PTA-10223, with a plant of another wheat line that comprises a desired trait to produce F1 progeny plants, wherein the desired trait is selected from the group consisting of male sterility, herbicide resistance, insect resistance, disease resistance and waxy starch;
   (b) selecting F1 progeny plants that have the desired trait to produce selected F1 progeny plants;
   (c) crossing the selected progeny plants with the E0028 plants to produce backcross progeny plants;
   (d) selecting for backcross progeny plants that have the desired trait and physiological and morphological characteristics of MSU Line E0028 to produce selected backcross progeny plants; and
   (e) repeating steps (c) and (d) three or more times in succession to produce selected fourth or higher backcross progeny plants that comprise the desired trait and all of the physiological and morphological characteristics of MSU Line E0028 as determined at the 5% significance level when grown in the same environmental conditions.

28. A plant produced by the method of claim 27, wherein the plant has the desired trait and all of the physiological and morphological characteristics of MSU Line E0028 as determined at the 5% significance level when grown in the same environmental conditions.

29. The wheat plant or a portion of the wheat plant of claim 28, wherein the desired trait is herbicide resistance and the resistance is conferred to an herbicide selected from the group consisting of imidazalinone, sulfonylurea, glyphosate, glufosinate, L-phosphinothricin, triazine and benzonitrile.

30. The wheat plant or a portion of the wheat plant of claim 28, wherein the desired trait is insect resistance and the insect resistance is conferred by a transgene encoding a *Bacillus thuringiensis* endotoxin.

31. The wheat plant or a portion of the wheat plant of claim 28, wherein the desired trait is disease resistance to *fusarium graminearum* and the disease resistance is conferred through the detoxification of deoxynivalenol.

32. The wheat plant or a portion of the wheat plant of claim 28, wherein the desired trait is male sterility and the trait is conferred by a cytoplasmic nucleic acid molecule that confers male sterility.

33. A method of modifying fatty acid metabolism, phytic acid metabolism, carbohydrate metabolism, waxy starch content, gluten content, or water stress tolerance in MSU Line E0028 comprising:
   (a) crossing E0028 plants grown from E0028 seed, representative seed of which has been deposited under ATCC Patent Deposit Designation PTA-10223, with plants of another wheat variety that comprise a nucleic acid molecule encoding a polypeptide selected from the group consisting of phytase, stearyl-ACP desaturase, fructosyltransferase, levansucrase, alpha-amylase, invertase, starch branching enzyme, glutenin, gliadin, mannitol-1-phosphate dehydrogenase and a late embryogenesis abundant (LEA) protein;
   (b) selecting F1 progeny plants that have said nucleic acid molecule to produce selected F1 progeny plants;
   (c) crossing the selected progeny plants with the E0028 plants to produce backcross progeny plants;
   (d) selecting for backcross progeny plants that have said nucleic acid molecule and physiological and morphological characteristics of MSU Line E0028 to produce selected backcross progeny plants; and
   (e) repeating steps (c) and (d) three or more times in succession to produce selected fourth or higher backcross progeny plants that comprise said nucleic acid molecule and have all of the physiological and morphological characteristics of MSU Line E0028 as determined at the 5% significance level when grown in the same environmental conditions.

34. A plant produced by the method of claim 33, wherein the plant comprises the nucleic acid molecule and has all of the physiological and morphological characteristics of MSU Line E0028 as determined at the 5% significance level when grown in the same environmental conditions.

* * * * *

UNITED STATES PATENT AND TRADEMARK OFFICE
CERTIFICATE OF CORRECTION

PATENT NO.       : 8,309,830 B2
APPLICATION NO.  : 12/763713
DATED            : November 13, 2012
INVENTOR(S)      : Richard W. Ward and Lee F. Siler It is certified that error appears in the above-identified patent and that said Letters Patent is hereby corrected as shown below:

In the Specifications:

Column 4, line 49, "F1's" should be --F1s--.

Column 6, line 48, after "production of" insert --hybrid--.

Column 8, line 46, "12214/B0246//" should be --I2214/B0246//--.

Column 10, line 26, "E. O, Speer" should be --E. O. Speer--.

Column 11, line 41, "tails" should be --talls--.

Column 11, line 46, ""Calcdonia." Calcdonia" should be --"Caledonia." Caledonia--.

Column 12, line 6, both occurrences of "Calcdonia" should be --Caledonia--.

Column 12, line 12, "Calcdonia" should be --Caledonia--.

Column 20, line 21, "Calcdonia" should be --Caledonia--.

Column 21, line 5, "Calcdonia" should be --Caledonia--.

Column 21, line 53, "*Stagonospora* tritici" should be --*Stagonospora tritici*--.

Column 22, line 64, after "would" insert --occur--.

Column 26, line 41, "'Calcdonia'" should be --'Caledonia'--.

Column 26, line 44, "(Calcdonia=5723 kg ha$^{-1}$)" should be --(Caledonia=5723 kg ha$^{-1}$)--.

Column 26, line 45, "fouryear" should be --four-year--.

Column 26, line 46, "LSD$_{p<0.5=0.9}$" should be --LSD$_{p<0.05}$ = 0.9--.

Column 27, line 38, "as well a" should be --as well as--.

Column 27, line 39, "Patton'" should be --'Patton'--.

Column 27, line 40, "INW0411'" should be --'INW0411'--.

Column 27, line 43, "74.8 kg h$^{-1}$" should be --74.8 kg hL$^{-1}$--.

Column 27, line 44, "73.8 kg h$^{-1}$" should be --73.8 kg hL$^{-1}$--.

Column 27, line 46, "Area 1" should be --Area I--.

Signed and Sealed this
Twenty-fifth Day of June, 2013

Teresa Stanek Rea
*Acting Director of the United States Patent and Trademark Office*

CERTIFICATE OF CORRECTION (continued)
U.S. Pat. No. 8,309,830 B2

Column 27, line 67, "Calcdonia" should be --Caledonia--.

Column 28, line 44, "table 17" should be --Table 17--.

Column 29, line 64, "eluded" should be --included--.

Column 31, line 4, "Calcdonia" should be --Caledonia--.

Column 31, line 8, "Calcdonia" should be --Caledonia--.

Column 31, line 11, "Calcdonia" should be --Caledonia--.

Column 31, line 14, "Calcdonia" should be --Caledonia--.

Column 31, line 59, "Calcdonia" should be --Caledonia--.

Column 33, line 28, "Mild B L" should be --Miki B L--.

Column 34, lines 1-2, "On G.A." should be --Orr G.A.--.

Column 35, line 48, "Jtine 24" should be --June 24--.

Column 36, line 1, "2004" should be --(2004)--.

Column 36, lines 57-58, "Phytopathol 28: 451" should be --Phytopathol. 28: 451--.

Column 37, line 21, "(O) Genes" should be --(Q) Genes--.

Column 37, line 53, delete second occurrence of "Plant Physiol".

Column 37, line 62, "Mild et al." should be --Miki et al.--.

Column 41, line 8, after "Falco et al.," insert --published--.

Column 41, lines 19-20, after "Falco et al.," insert --published--.

Column 42, line 6, "FLP/PRT" should be --FLP/FRT--.

Column 42, line 15, "pSRi" should be --pSR1--.

Column 43, line 22, "Mar. 30, 20044 ($F_7$)" should be --Mar. 30, 2004 (FT)--.

Column 44, line 29, "Mild et al." should be --Miki et al.--.

Column 46, line 27, "made-up" should be --made up--.

Column 46, line 36, "$F_2$" should be --F2--.

UNITED STATES PATENT AND TRADEMARK OFFICE
CERTIFICATE OF CORRECTION

| | | |
|---|---|---|
| PATENT NO. | : 8,309,830 B2 | Page 1 of 1 |
| APPLICATION NO. | : 12/763713 | |
| DATED | : November 13, 2012 | |
| INVENTOR(S) | : Richard W. Ward et al. | |

It is certified that error appears in the above-identified patent and that said Letters Patent is hereby corrected as shown below:

In the Specification:
Column 1 Line 11 delete:

"GOVERNMENT RIGHTS

This invention was made with support in part by the U.S. Department of Agriculture, under Agreement No. 59-0790-6-061, where the invention is a cooperative project with the U.S. Wheat & Barley Scab Initiative. The U.S. Government has certain rights in the invention."

and insert therefor:

--GOVERNMENT LICENSE RIGHTS

This invention was made with government support under 59-0790-6-061 awarded by the U.S. Department of Agriculture. The government has certain rights in the invention.--

Signed and Sealed this
Fifth Day of August, 2014

Michelle K. Lee
*Deputy Director of the United States Patent and Trademark Office*